(12) United States Patent
Osaki et al.

(10) Patent No.: US 11,318,101 B2
(45) Date of Patent: May 3, 2022

(54) HARD CAPSULE HAVING IMPROVED HARDNESS, AND METHOD FOR MANUFACTURING SAME

(71) Applicant: QUALICAPS CO., LTD., Nara (JP)

(72) Inventors: Yoshiro Osaki, Nara (JP); Toshimitsu Usui, Nara (JP); Makoto Aso, Nara (JP)

(73) Assignee: QUALICAPS CO., LTD., Nara (JP)

( * ) Notice: Subject to any disclaimer, the term of this patent is extended or adjusted under 35 U.S.C. 154(b) by 485 days.

(21) Appl. No.: 16/314,728

(22) PCT Filed: Jul. 4, 2017

(86) PCT No.: PCT/JP2017/024564
§ 371 (c)(1),
(2) Date: Jan. 2, 2019

(87) PCT Pub. No.: WO2018/008660
PCT Pub. Date: Jan. 11, 2018

(65) Prior Publication Data
US 2021/0196640 A1 Jul. 1, 2021

(30) Foreign Application Priority Data
Jul. 6, 2016 (JP) .............................. JP2016-134353

(51) Int. Cl.
*A61K 9/48* (2006.01)
*A61K 47/02* (2006.01)
*A61K 47/32* (2006.01)
*A61K 47/38* (2006.01)

(52) U.S. Cl.
CPC ............ *A61K 9/4816* (2013.01); *A61K 47/02* (2013.01); *A61K 47/32* (2013.01); *A61K 47/38* (2013.01)

(58) Field of Classification Search
CPC ...... A61K 9/4816; A61K 47/02; A61K 47/32; A61K 47/38
See application file for complete search history.

(56) References Cited

U.S. PATENT DOCUMENTS

| | | | |
|---|---|---|---|
| 2,526,683 A | 10/1950 | Murphy | |
| 2,718,667 A | 9/1955 | Malm et al. | |
| 3,508,678 A | 4/1970 | Graham et al. | |
| 3,617,588 A | 11/1971 | Langman | |
| 3,823,843 A | 7/1974 | Stephens et al. | |
| 4,040,536 A | 8/1977 | Schwarz | |
| 4,069,819 A | 1/1978 | Valentini et al. | |
| 4,210,140 A | 7/1980 | James et al. | |
| 4,365,060 A | 12/1982 | Onda et al. | |
| 4,591,475 A | 5/1986 | Tomka et al. | |
| 4,822,618 A | 4/1989 | Schweiger et al. | |
| 4,993,137 A | 2/1991 | Muto et al. | |
| 5,032,074 A | 7/1991 | Muto et al. | |
| 5,431,917 A | 7/1995 | Yamamoto et al. | |
| 5,756,123 A | 5/1998 | Yamamoto et al. | |
| 5,769,267 A | 6/1998 | Duynslager et al. | |
| 6,499,279 B1 | 12/2002 | Yamamoto et al. | |
| 6,517,865 B2 | 2/2003 | Cade et al. | |
| 6,649,180 B1 | 11/2003 | Matsuura et al. | |
| 6,967,026 B2 | 11/2005 | Hoshi et al. | |
| 7,255,921 B2 | 8/2007 | Kamaguchi et al. | |
| 7,669,596 B2 | 3/2010 | Alston | |
| 9,138,920 B2 | 9/2015 | De Bock et al. | |
| 9,211,659 B2 | 12/2015 | De Bock et al. | |
| 2001/0036471 A1* | 11/2001 | Angel | A61K 9/4816 424/451 |
| 2002/0187190 A1 | 12/2002 | Cade et al. | |
| 2003/0166763 A1 | 9/2003 | Hoshi et al. | |
| 2005/0037064 A1* | 2/2005 | Basquin | C08L 5/14 424/451 |
| 2005/0069579 A1 | 3/2005 | Kamaguchi et al. | |
| 2005/0186268 A1 | 8/2005 | Hoshi et al. | |
| 2007/0065501 A1 | 3/2007 | He et al. | |
| 2008/0008750 A1 | 1/2008 | Tochio et al. | |
| 2010/0168410 A1 | 7/2010 | Cade et al. | |
| 2010/0233252 A1 | 9/2010 | Tochio et al. | |
| 2010/0300440 A1 | 12/2010 | Deboeck et al. | |
| 2012/0022169 A1 | 1/2012 | Moriuchi et al. | |
| 2015/0118298 A1* | 4/2015 | Zhang | A61K 31/122 424/456 |
| 2019/0282509 A1* | 9/2019 | Osaki | A61K 9/4816 |

FOREIGN PATENT DOCUMENTS

| | | | |
|---|---|---|---|
| CA | 1 238 738 | 6/1988 | |
| CN | 1687203 | 10/2005 | |
| CN | ON 103690510 | * 4/2014 | ............... A61K 9/48 |
| CN | 104224746 | 12/2014 | |
| EP | 3 485 911 | 5/2019 | |

(Continued)

OTHER PUBLICATIONS

CN 103690510 machine translation (Year: 2014).*

(Continued)

*Primary Examiner* — Sean M Basquill
(74) *Attorney, Agent, or Firm* — Wenderoth, Lind & Ponack, L.L.P.

(57) ABSTRACT

An object of the present invention is to improve the hardness of the capsule film of a hard capsule. The present invention improves the hardness of the capsule film of a hard capsule by adding a starch decomposition product, and/or at least one clay mineral selected from the group consisting of talc, bentonite, and kaolin, to a hard capsule film.

19 Claims, 2 Drawing Sheets

(56) References Cited

FOREIGN PATENT DOCUMENTS

| | | |
|---|---|---|
| JP | 01-40626 | 8/1989 |
| JP | 02-028260 | 1/1990 |
| JP | 05-39777 | 6/1993 |
| JP | 6-179618 | 6/1994 |
| JP | 11-510148 | 9/1999 |
| JP | 2000-508552 | 7/2000 |
| JP | 2000-226097 | 8/2000 |
| JP | 2001-506692 | 5/2001 |
| JP | 2004-167084 | 6/2004 |
| JP | 3592723 | 11/2004 |
| JP | 2005-509052 | 4/2005 |
| JP | 2005-187412 | 7/2005 |
| JP | 2005-194218 | 7/2005 |
| JP | 3670016 | 7/2005 |
| JP | 2005-526758 | 9/2005 |
| JP | 3726570 | 12/2005 |
| JP | 2006-131673 | 5/2006 |
| JP | 2007-144014 | 6/2007 |
| JP | 2007-308713 | 11/2007 |
| JP | 2007-530726 | 11/2007 |
| JP | 2009-504630 | 2/2009 |
| JP | 2010-270039 | 12/2010 |
| JP | 5072358 | 11/2012 |
| JP | 2015-40186 | 3/2015 |
| JP | 2015-517554 | 6/2015 |
| WO | 96/18370 | 6/1996 |
| WO | 97/04755 | 2/1997 |
| WO | 97/37629 | 10/1997 |
| WO | 98/27151 | 6/1998 |
| WO | 99/46329 | 9/1999 |
| WO | 02/17848 | 3/2002 |
| WO | 03/075909 | 9/2003 |
| WO | 2005/009380 | 2/2005 |
| WO | 2005/092968 | 10/2005 |
| WO | 2006/070578 | 7/2006 |
| WO | 2007/020529 | 2/2007 |
| WO | 2009/125483 | 10/2009 |
| WO | 2010/114134 | 10/2010 |
| WO | 2013/174921 | 11/2013 |
| WO | 2018/008660 | 1/2018 |
| WO | 2018/043661 | 3/2018 |

OTHER PUBLICATIONS

Office Action dated Jan. 5, 2021 in the corresponding Indian Patent Application No. 201947003671.
International Search Report dated Nov. 12, 2019 in International (PCT) Application No. PCT/JP2019/038836.
International Search Report dated Nov. 12, 2019 in International (PCT) Application No. PCT/JP2019/038838.
International Search Report dated Aug. 22, 2017 in International (PCT) Application No. PCT/JP2017/024564 with English translation.
Al-Tabakha, "HPMC Capsules: Current Status and Future Prospects", J Pharm Pharmaceut Sci, vol. 13, No. 3, pp. 428-442, 2010.

* cited by examiner

HARD CAPSULE HAVING IMPROVED HARDNESS, AND METHOD FOR MANUFACTURING SAME

TECHNICAL FIELD

The present invention relates to a hard capsule with improved hardness, and a method for producing the hard capsule.

BACKGROUND ART

Hard capsules have a long history as a technique of oral preparation; and are highly convenient in that they are capable of encapsulating a wide variety of contents by as simple a method as possible, and delivering the contents to users.

"Runnability" refers to ease of operability upon encapsulation of a content into a hard capsule, or upon placing a hard capsule with a content encapsulated therein into an outer package material. When the capsules are handled with a high-speed filling device, local adsorption or pressing may occur, and may cause deformation of the capsules due to local stress. The degree of deformation depends on the hardness of the capsule film. If the capsule film is hard, the degree of deformation will be small, and speedier and more stable handling are possible; in other words, the runnability increases. Further, when excessive local stress is instantaneously exerted on a hard capsule, excessive local deformation occurs, which may result in breakage of the capsule. The runnability also increases as the brittleness decreases. Additionally, a hard capsule, which is hard and does not easily break, has a small risk of breakage; or a small risk of subsequent leakage or splattering of the content upon transportation, or when the user touches it with their hands. Such easy handling and convenience of hard capsules are considered advantageous.

There are safety restrictions on the polymer materials usable for pharmaceutical products or food capsule compositions; therefore, methods for improving hardness or breakage resistance by increasing the degree of crosslinking, or increasing the crosslinking-inducing reactivity, cannot be adopted. However, the breakage resistance may be improved relatively easily regardless of the capsule hardness, without changing the structure of the polymer material used as a major ingredient, by a method of controlling molecular weight having a smaller influence on safety. This method is generally performed by increasing the molecular weight to enhance the entanglement of the main chains. On the other hand, since the hardness of the polymer material hardly depends on the molecular weight once the ratio of the backbone and the substituents in the polymer material of the capsule film is fixed, it is difficult to improve the capsule hardness by molecular weight control.

Further, mixed materials obtained by mixing different polymer materials are often not suitable as a hard capsule material due to their insufficient compatibility, or undesirable capsule moldability.

On the other hand, it may be possible to add some additives, preferably highly safe additives with relatively low molecular weight that are approved as pharmaceutical or food additives; however, a material that enables significant improvement in capsule film hardness is as of yet unknown.

In the first place, if the major ingredient of the material is incapable of forming a flat and continuous film with a thickness of about 100 μm, which is suitable for a hard capsule, the material is not suitable as a hard capsule film material. Further, when a large amount of commonly used inorganic filler is added, as mentioned above, it is difficult to obtain a flat film having a uniform thickness of about 100 μm. It also poses safety concerns.

Since it is necessary to select the major ingredient of the capsule film on the premise of selecting a suitable combination of a polymer material and additives for a hard capsule film, and improving the hardness of the capsule, the simple use of a hardness improving method for a general polymer material with no modification is clearly insufficient.

Hard capsules containing, as a major ingredient, a cellulose compound, such as hydroxypropylmethylcellulose, are advantageous in that they are chemically stable and have a low moisture content; they also ensure breakage resistance to some extent even under low humidity, compared with gelatin capsules commonly used as hard capsules. On the other hand, since cellulose compounds are slightly inferior to gelatin capsules in terms of hardness, it is necessary to improve the hardness of the capsule film (Non-Patent Document 1).

CITATION LIST

Non-Patent Documents

Non-Patent Document 1: Moawia M. Al-Tabakha: J Phaim Pharmaceut Sci (www.cspsCanada.org) 13(3) 428-442, 2010

SUMMARY OF INVENTION

Technical Problem

In addition, since hard capsules containing polyvinyl alcohol as a major ingredient soften in an environment with a relative humidity of more than about 50%, it is necessary to improve the hardness of the capsule film so as to retain a certain degree of hardness under such an environment.

Further, when a hard capsule is used as an inhalation capsule preparation, a single dose of the drug is sealed in the hard capsule, and the capsule is pierced with a small pin to enable inhalation of the drug inside at an appropriate flow rate. In this case, the capsule film does not have to be readily soluble; however, excessive capsule deformation by pressing with a pin, or extension of cracks or breakage from the hole or periphery thereof may undesirably occur. This may cause broken pieces of the capsule film to be mixed with the inhalation preparation inside the capsule, or may result in a failure to discharge a stable amount of the drug. Thus, in order to form a small hole with a clear outline, appropriate hardness and breakage resistance (toughness) are required when a hole is made with a pin.

An object of the present invention is to improve the hardness of the capsule film of a hard capsule, in order to ensure superior runnability and hardness according to need.

Solution to Problem

The inventors of the present invention conducted extensive research, and found that the hardness of a hard capsule can be improved by adding a starch decomposition product to a hard capsule base. The inventors further found that the hardness of the capsule film of a hard capsule can be improved by adding at least one clay mineral selected from the group consisting of talc, bentonite, and kaolin to a hard capsule base.

The present invention was completed based on the above findings, and encompasses the following embodiments.

I-1-1. A hard capsule comprising a film containing a base and a hardness improving agent, the base being at least one member selected from the group consisting of cellulose compounds, polyvinyl alcohol, and polyvinyl alcohol copolymers; and the hardness improving agent being at least one member selected from the group consisting of starch decomposition products having a DE value of more than 11 and less than 40, and two or more kinds of starch decomposition product combined to have a calculated DE value of more than 11 and less than 40 (provided that the two or more kinds of starch decomposition product exclude starch decomposition products solely having a DE value of 5 or less, and monosaccharides).

I-1-2. The hard capsule according to item I-1-1, wherein the hardness improving agent is two or more kinds of starch decomposition product, and the two or more kinds of starch decomposition product are selected from starch decomposition products having a DP value of more than 5 and not more than 50.

I-1-3. The hard capsule according to item I-1-1 or I-1-2, wherein the amount of the hardness improving agent contained in the hard capsule is 10 to 30 wt % based on 100 wt % of the total film components of the hard capsule, excluding moisture.

I-1-4. The hard capsule according to any one of items I-1-1 to I-1-3, further comprising a gelling agent, or a gelling agent and a gelling aid.

I-1-5. The hard capsule according to item I-1-4, wherein the gelling agent is κ-carrageenan, and the gelling aid is potassium chloride.

I-1-6. The hard capsule according to any one of items I-1-1 to I-1-5, further comprising a plasticizer and/or a light shielding agent.

I-1-7. The hard capsule according to any one of items I-1-1 to I-1-6, wherein the hard capsule further comprises at least one member selected from the group consisting of bentonite, talc, and kaolin.

I-2-1. A hard capsule-preparing solution comprising a base and a hardness improving agent, the base being at least one member selected from the group consisting of cellulose compounds, polyvinyl alcohol, and polyvinyl alcohol copolymers; and the hardness improving agent being at least one member selected from the group consisting of starch decomposition products having a DE value of more than 11 and less than 40, and two or more kinds of starch decomposition product combined to have a calculated DE value of more than 11 and less than 40 (provided that the two or more kinds of starch decomposition product exclude starch decomposition products solely having a DE value of 5 or less, and monosaccharides).

I-2-2. The hard capsule-preparing solution according to item I-2-1, wherein the hardness improving agent is two or more kinds of starch decomposition product, and the two or more kinds of starch decomposition product are selected from starch decomposition products having a DP value of more than 5 and not more than 50.

I-2-3. The hard capsule-preparing solution according to item I-2-1 or I-2-2, wherein the amount of the hardness improving agent contained in the hard capsule is 10 to 30 wt % based on 100 wt % of the total components of the preparing solution, excluding solvent.

I-2-4. The hard capsule-preparing solution according to any one of items I-2-1 to I-2-3, further comprising a gelling agent, or a gelling agent and a gelling aid.

I-2-5. The hard capsule-preparing solution according to item I-2-4, wherein the gelling agent is κ-carrageenan, and the gelling aid is potassium chloride.

I-2-6. The hard capsule-preparing solution according to any one of items I-2-1 to I-2-5, further comprising a plasticizer and/or a light shielding agent.

I-2-7. The hard capsule-preparing solution according to any one of items I-2-1 to I-2-6, wherein the hard capsule further comprises at least one member selected from the group consisting of bentonite, talc, and kaolin.

I-3-1. A method for preparing a hard capsule, comprising the step of:

preparing a hard capsule by using the hard capsule-preparing solution according to any one of items I-2-1 to I-2-7.

I-3-2. The method for preparing a hard capsule according to item I-3-1, wherein the method for preparing a hard capsule is a cold gelation method.

I-3-2. The method for preparing a hard capsule according to item I-3-1 or I-3-2, wherein the method for preparing a hard capsule is a method for improving the hardness of a hard capsule.

II-1-1. A hard capsule comprising a film containing a base and a hardness improving agent, (i) the base being at least one member selected from the group consisting of cellulose compounds, polyvinyl alcohol, and polyvinyl alcohol copolymers;

the hardness improving agent being at least one member selected from the group consisting of talc, bentonite, and kaolin;

the amount of talc contained in the hard capsule being more than 10 wt % and not more than 50 wt % based on 100 wt % of the total film components of the hard capsule, excluding moisture;

the amount of bentonite contained in the hard capsule being more than 0.5 wt % and less than 10 wt % based on 100 wt % of the total film components of the hard capsule, excluding moisture; and the amount of kaolin contained in the hard capsule being not less than 10 wt % and not more than 50 wt % based on 100 wt % of the total film components of the hard capsule, excluding moisture.

II-1-2. The hard capsule according to item II-1-1, further comprising a gelling agent, or a gelling agent and a gelling aid.

II-1-3. The hard capsule according to item II-1-2, wherein the gelling agent is κ-carrageenan, and the gelling aid is potassium chloride.

II-1-4. The hard capsule according to any one of items II-1-1 to II-1-3, further comprising a plasticizer and/or a light shielding agent.

II-2-1. A hard capsule-preparing solution comprising a base and a hardness improving agent, (i) the base being at least one member selected from the group consisting of cellulose compounds, polyvinyl alcohol, and polyvinyl alcohol copolymers;

the hardness improving agent being at least one member selected from the group consisting of talc, bentonite, and kaolin;

the amount of talc contained in the hard capsule being more than 10 wt % and not more than 50 wt % based on 100 wt % of the total components of the preparing solution, excluding solvent;

the amount of bentonite contained in the hard capsule is more than 0.5 wt % and less than 10 wt % based on 100 wt % of the total components of the preparing solution, excluding solvent; and the amount of kaolin contained in the hard capsule being not less than 10 wt % and not more than 50 wt % based on 100 wt % of the total components of the preparing solution, excluding solvent.

II-2-2. The hard capsule-preparing solution according to item II-2-1, further comprising a gelling agent, or a gelling agent and a gelling aid.

II-2-3. The hard capsule-preparing solution according to item II-2-2, wherein the gelling agent is κ-carrageenan, and the gelling aid is potassium chloride.

II-2-4. The hard capsule-preparing solution according to any one of items II-2-1 to II-2-3, further comprising a plasticizer and/or a light shielding agent.

II-3-1. A method for preparing a hard capsule, comprising the step of:

preparing a hard capsule by using the hard capsule-preparing solution according to any one of items II-2-1 to II-2-4.

I-3-2. The method for preparing a hard capsule according to item II-3-1, wherein the method for preparing a hard capsule is a cold gelation method.

II-3-3. The method for preparing a hard capsule according to item II-3-1 or I-3-2, wherein the method for preparing a hard capsule is a method for improving the hardness of a hard capsule.

Advantageous Effects of Invention

The present invention provides a hard capsule with improved hardness, and a method for preparing the hard capsule.

BRIEF DESCRIPTION OF DRAWINGS

FIG. 1 shows a film set in an Autograph.

FIG. 2 shows a state in which a metal indenter compresses the film top.

FIG. 3 shows a state of hardness measurement for a hard capsule.

DESCRIPTION OF EMBODIMENTS

Figure 1A:
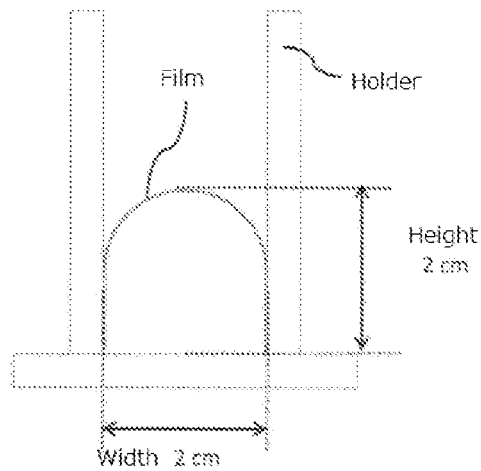
FIG. 1(a) is a front view.
Figure 1B:
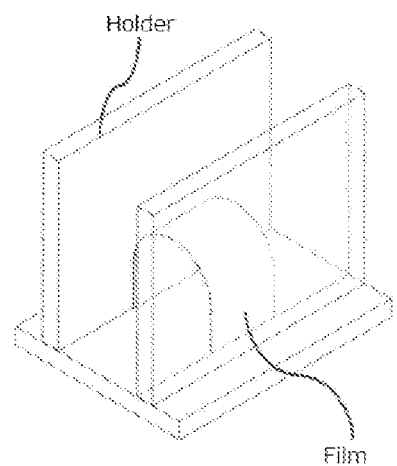
FIG. 1(b) is a perspective view.

1. Explanation of Terms (1) Hard Capsule Material

First, terms for use in this specification, claims, etc., are explained. The terms used in the present invention are as explained in this section, unless otherwise specified.

In the present invention, "hard capsule" refers to a type of capsule that is produced by first producing a capsule film, and then encapsulating content in the capsule shell film (the capsule film) produced. The capsule is usually composed of a cap portion and a body portion, and is also called a hard capsule or a two-piece capsule. The "hard capsule" of the present invention does not encompass soft capsules, which are produced by placing content between two sheets of film and then adhering the two sheets of film to each other; seamless capsules, which are produced by dropwise adding content with a film solution to a solidification liquid; or microcapsules, which are prepared by incorporating an active ingredient inside via base material deposition or emulsification.

In the present invention, the "base" refers to a main component for forming a hard capsule film. Preferably, the base is hydrophilic; can easily be dissolved in the digestive system; form a capsule shell (form a film) with an appropriate strength, i.e., hardness and breakage resistance, after drying; and is a chemically stable polymer material. Since safety and stability suitable for pharmaceuticals and food compositions are required, highly reactive or highly cross-linkable materials are not preferable. As a hydrophilic polymer used in the present invention, for example, at least one member selected from the group consisting of cellulose compounds, polyvinyl alcohol (PVA), and polyvinyl alcohol copolymers (PVA copolymers) can be used.

Examples of cellulose compounds that can be used in the present invention include water-soluble cellulose ethers in which one or more hydrogen atoms of hydroxyl groups of cellulose are replaced with at least one substituent selected from the group consisting of alkyl groups and hydroxyalkyl groups. Examples of the "alkyl groups" in the alkyl groups and hydroxyalkyl groups include linear or branched lower alkyl groups having 1 to 6 carbon atoms, and preferably 1 to 4 carbon atoms. Specific examples include methyl, ethyl, butyl, and propyl. Specific examples of water-soluble cellulose compounds include lower alkyl celluloses, such as methyl cellulose; hydroxy-lower alkyl celluloses, such as hydroxyethylcellulose and hydroxypropyl cellulose; and hydroxy-lower alkylalkyl celluloses, such as hydroxyethylmethylcellulose, hydroxyethylethylcellulose, and hydroxypropylmethylcellulose (herein sometimes also referred to as hypromellose or HPMC). Among these, hydroxypropylmethylcellulose is the most preferable cellulose compound because of its film-forming properties and excellent mechanical strength under low-moisture conditions. Examples of application of a cellulose compound to a hard capsule include those disclosed in U.S. Pat. Nos. 2,526,683, 2,718,667, 3,617,588, 4,365,060, 4,993,137, 5,032,074, 5,431,917, 5,756,123, 6,517,865, 6,649,180, U.S. Patent No. 2010/0168410, U.S. Pat. Nos. 9,138,920, and 9,211,659.

The hydroxypropylmethylcellulose that can be used in the present invention includes the hypromellose shown in Table 1, which is prescribed in the Japanese Pharmacopoeia.

TABLE 1

| Degree-of-substitution type | Methoxy group (%) | | Hydroxypropyl group (%) | |
|---|---|---|---|---|
| | Lower limit | Upper limit | Lower limit | Upper limit |
| 1828 | 16.5 | 20.0 | 23.0 | 32.0 |
| 2208 | 19.0 | 24.0 | 4.0 | 12.0 |
| 2906 | 27.0 | 30.0 | 4.0 | 7.5 |
| 2910 | 28.0 | 30.0 | 7.0 | 12.0 |

Further, the hydroxypropylmethylcellulose of the present invention includes hypromellose having the following molecular weight, which has been approved for use as a food additive in Japan.

Molecular Weight

Unsubstituted structural units: 162.14 Substituted structural units: about 180 (degree of substitution: 1.19), about 210 (degree of substitution: 2.37) Polymer: about 13,000 (n=about 70) to about 200,000 (n=about 1000).

Commercially available hydroxypropylmethylcellulose typically has a weight average molecular weight (Mw)/number average molecular weight (Mn) (Mw/Mn) ratio within the range of 1.5 to 4. The weight average molecular weight (Mw) and the number average molecular weight (Mn) used to calculate this ratio (Mw/Mn) can both be determined by gel chromatography (size exclusion chromatography). The principle and method of the gel chromatography are not limited. For example, reference can be made to the description in "The United States Pharmacopeia: USP30/The National Formulary: NF25," chapter "Chromatography," section "Size-Exclusion Chromatography."

Examples of commercially available hydroxypropylmethylcellulose include the TC-5 series, the SB-4(Trademark) series, and the METOLOSE(Trademark) series of Shin-Etsu Chemical Co., Ltd., the AnyCoat-C(Trademark) series of Lotte (formerly Samsung) Precision Chemistry Co. Ltd., and the Methocel(Trademark) series of The Dow Chemical Company.

Further, the hypromellose used in the present invention includes hypromellose having a viscosity of 3 to 50 mPa·s as measured at 20° C.±0.1° C. in the form of a 2 wt % aqueous solution of hypromellose.

In the present invention, hypromellose can be used singly, or in a combination of two or more. In any case, hypromellose having a "hypromellose viscosity value" within the range of 300 to 5000, preferably 300 to 1500, and more preferably 300 to 960 can be preferably used. The "hypromellose viscosity value" refers to the sum of products obtained by multiplying the viscosity of each hypromellose used to prepare a capsule film, as measured at 20° C.±0.1° C. in the form of a 2 wt % aqueous solution of hypromellose, by the proportion (parts by weight) of each hypromellose, based on 100 parts by weight of the total hypromellose amount. More specifically, when hypromellose having a viscosity of 6 mPa·s as measured in the form of a 2 wt % aqueous solution of hypromellose is used alone to produce a capsule film, the "hypromellose viscosity value" is 600, which is obtained by the following calculation: 6 mPa·s×100 parts by weight. When 30 parts by weight of hypromellose having a viscosity of 4 mPa·s and 70 parts by weight of hypromellose having a viscosity of 6 mPa·s, as measured in the form of a 2 wt % aqueous solution of hypromellose, are used in combination to produce a capsule film, the "hypromellose viscosity value" is 540, which is obtained by the following calculation: 4 mPa·s×30 parts by weight+6 mPa·s×70 parts by weight.

In general, a lower molecular weight leads to a lower viscosity. A low molecular weight, i.e., a low viscosity, provides better solubility of hard capsules; however, hard capsules with a low viscosity tend to be easily broken.

Accordingly, for oral pharmaceutical products in which good solubility is important, the viscosity is preferably 300 to 960. On the other hand, for inhalation drugs or foods in which breakage resistance is important, the viscosity is preferably 500 to 1500.

PVA refers to a polymer obtained by saponification of polyvinyl acetate. In general, there are two types of PVA: fully saponified PVA with a saponification degree of 97 mol % or more, which is represented by Formula (1) below; and partially saponified PVA with a saponification degree of 78 to 96 mol %, which is represented by Formula (2) below. In the present invention, both types of PVA, i.e., fully saponified PVA and partially saponified PVA, are usable. Although the degree of saponification is not particularly limited, a partially saponified PVA with a saponification degree of 78 to 90 mol %, particularly about 87 to 90 mol %, is preferably used.

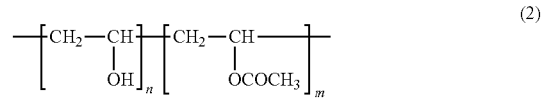

(wherein n and m each represent any integer).

The average degree of polymerization (n) of PVA is not particularly limited, as long as PVA can form a film. In general, PVA preferably has an average degree of polymerization of about 400 to 3300, and particularly preferably about 400 to 2000. The weight average molecular weight of PVA, calculated from the above average degree of polymerization and saponification degree, is about 18000 to about 175000. However, the weight average molecular weight is not particularly limited thereto.

Examples of PVA copolymers include PVA copolymers obtained by copolymerizing the above-mentioned PVA or PVA derivative(s) with a polymerizable vinyl monomer. Examples of PVA derivatives include known PVA derivatives, such as amine-modified PVA, ethylene-modified PVA, and PVA having thiol group(s) at end(s) thereof (terminally thiolated PVA). Terminally thiolated PVA is preferable.

Examples of polymerizable vinyl monomers include (1) acrylic acid, methacrylic acid, fumaric acid, maleic acid, and itaconic acid; (2) sodium salts, potassium salts, ammonium salts, and alkylamine salts of the compounds described above in (1); (3) methyl methacrylate, methyl acrylate, ethyl methacrylate, ethyl acrylate, butyl methacrylate, butyl acrylate, isobutyl methacrylate, isobutyl acrylate, cyclohexyl methacrylate, cyclohexyl acrylate, 2-ethylhexyl methacrylate, 2-ethylhexyl acrylate, acrylonitrile, acrylamide, dimethylacrylamide, styrene, vinyl acetate, hydroxyethyl methacrylate, hydroxyethyl acrylate, esters of polyethylene glycol and methacrylic acid, esters of polyethylene glycol and acrylic acid, esters of polypropylene glycol and methacrylic acid, esters of polypropylene glycol and acrylic acid, N-vinylpyrrolidone, and acryloyl morpholine; (4) compounds represented by the formula:

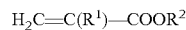

(wherein $R^1$ is a hydrogen atom or a methyl group, and $R^2$ is a hydrogen atom or an alkyl group having 1 to 4 carbon atoms).

The polymerizable vinyl monomer is preferably a combination of at least one compound selected from the group consisting of the compounds described in (1) and (2), and at least one compound selected from the group consisting of the compounds described in (3). A combination of acrylic acid or methacrylic acid with methyl methacrylate is particularly preferable.

The PVA copolymer is preferably a high-molecular-weight copolymer comprising a partially saponified PVA as the skeleton, and is produced by copolymerizing the PVA with acrylic acid and methyl methacrylate. More preferably, the PVA copolymer is a PVA copolymer produced by copolymerizing a partially saponified PVA having an average degree of polymerization of about 300 to 500 with a polymerizable vinyl monomer as described above (in particular, acrylic acid and methyl methacrylate) in a weight ratio in the range of about 6:4 to 9:1. As polymerizable vinyl monomers, acrylic acid and methyl methacrylate are preferably used in an acrylic acid:methyl methacrylate ratio by weight in the range of about 3:7 to 0.5:9.5 to form a copolymer with a partially saponified PVA. A PVA copolymer produced by copolymerizing a partially saponified PVA having an average degree of polymerization of 300 to 500, methyl methacrylate, and acrylic acid in a ratio (by weight) of 60 to 90:7 to 38:0.5 to 12 is particularly preferable.

Examples of commercially available PVA copolymers include the POVACOAT (Registered Trademark) series (Nissin Kasei Co., Ltd.).

Examples of application of PVA or a PVA copolymer to hard capsules include those disclosed in WO02/17848, WO1999/046329, WO2009/125483, and U.S. Pat. No. 6,967,026.

In the present invention, PVA and PVA copolymer(s) may be used in combination. The mixing ratio of the PVA to the PVA copolymer is not particularly limited. The PVA:PVA copolymer mixing ratio (by weight) may be in the range of 100:0 to 0:100, and preferably 99.9:0.1 to 0.1:99.9.

In the present invention, the "hardness improving agent" is a component that can improve the hardness of a capsule film after preparation. One component, or two or more components, may be used as the hardness improving agent. When the hardness improving agent comprises two or more components, these two or more components may be mixed beforehand, and then dissolved in a solvent for a capsule-preparing solution; or may be individually dissolved in a solvent for a capsule-preparing solution; or may be individually dissolved in a solvent for a capsule-preparing solution, and then mixed together. The hardness improving agent used in the present invention preferably does not impair general properties, such as safety necessary for use in pharmaceutical products or food compositions; chemical stability (avoidance of reactions with contents); storage stability (change with time); light shielding property; low oxygen permeability; low water vapor permeability; low water content; and constant charge.

The hard capsule of the present invention may comprise, in addition to the base and the hardness improving agent, a gelling agent, a gelling aid, a plasticizer, a lubricant, a sequestrant, a colorant, a light shielding agent, residual moisture (also simply referred to as moisture), etc.

Examples of gelling agents include carrageenan, tamarind seed polysaccharide, pectin, xanthan gum, locust bean gum, curdlan, gelatin, furcellaran, agar, gellan gum, and the like. These can be used singly, or in a combination of two or more.

Among the above gelling agents, carrageenan has a high gel strength. Furthermore, carrageenan, even when used in a small amount, can provide an excellent gelation effect in the presence of specific ions. Therefore, carrageenan is the most preferable gelling agent. In general, three types of carrageenan are known: kappa-carrageenan, iota-carrageenan, and lambda-carrageenan. In the present invention, kappa-carrageenan and iota-carrageenan with relatively high hardness and gelation ability can be preferably used. Pectin can be classified into LM pectin and HM pectin, according to the difference in the degree of esterification. Gellan gum can also be classified into acylated gellan gum (native gellan gum) and deacylated gellan gum according to the presence or absence of acylation. In the present invention, any of the above can be used, regardless of type.

When the hard capsule used in the present invention comprises the gelling agent, its content may be, for example, 0.05 to 10 wt %, preferably 0.1 to 9.5 wt %, more preferably 0.2 to 9 wt %, and even more preferably 0.3 to 8 wt %, based on 100 wt % of the total hard capsule film components, excluding moisture.

A gelling aid can also be used according to the type of gelling agent used. When carrageenan is used as a gelling agent, for example, the following gelling aids can be used in combination with carrageenan. For kappa-carrageenan, examples of usable gelling aids include compounds capable of donating at least one type of ion selected from potassium ion, ammonium ion, and calcium ion, such as potassium chloride, potassium phosphate, ammonium chloride, ammonium acetate, and calcium chloride. For iota-carrageenan, examples of usable gelling aids include compounds capable of donating calcium ions in water, such as calcium chloride. When gellan gum is used as a gelling agent, examples of gelling aids that can be used in combination with the gelling agent include compounds capable of donating in water at least one ion selected from sodium ions, potassium ions, and calcium ions, such as sodium chloride, potassium chloride, calcium chloride, and magnesium sulfate. In addition, as an organic acid or a water-soluble salt thereof, citric acid or sodium citrate can also be used.

When the hard capsule of the present invention comprises a gelling aid, such as potassium chloride, its content may be, for example, in the range of 2.2 wt % or less, preferably 0.1 to 2.1 wt %, more preferably 0.2 to 1.9 wt %, and even more preferably 0.3 to 1.6 wt %, based on 100 wt % of the total hard capsule film components, excluding moisture.

When hydroxypropylmethylcellulose is used as a cellulose compound, the gelling agent that can be preferably used in combination with hydroxypropylmethylcellulose is, for example, carrageenan, particularly preferably kappa-carrageenan, and the gelling aid that can be preferably used with such carrageenan is, for example, potassium chloride.

Any plasticizers can be used without limitation insofar as they can be used in pharmaceutical products or food compositions. Examples of usable plasticizers include dioctyl adipate, adipic acid polyester, epoxidated soybean oil, diester of epoxyhexahydrophthalic acid, kaolin, triethyl citrate, glycerol, glycerol fatty acid ester, sesame oil, a mixture of dimethylpolysiloxane and silicon dioxide, D-sorbitol, medium-chain triglyceride, corn starch-derived liquid sugar alcohol, triacetin, concentrated glycerin, castor oil, phytosterol, diethyl phthalate, dioctyl phthalate, dibutyl phthalate, butyl phthalyl butyl glycolate, propylene glycol, polyoxyethylene (105) polyoxypropylene (5) glycol, Polysorbate 80, Macrogol 1500, Macrogol 400, Macrogol 4000, Macrogol 600, Macrogol 6000, isopropyl myristate, a mixture of cottonseed oil and soybean oil, glyceryl monostearate, and isopropyl linoleate. When a plasticizer is used, the amount of plasticizer added may be, for example, typically in the range of 15 wt % or less, preferably 13 wt % or less, more preferably 11 wt % or less, and even more preferably 8 wt % or less, based on 100 wt % of the total hard capsule film components, excluding moisture.

Examples of sequestrants include ethylenediaminetetraacetic acid, acetic acid, boric acid, citric acid, gluconic acid, lactic acid, phosphoric acid, tartaric acid, or salts of these acids, metaphosphate, dihydroxyethylglycine, lecithin, β-cyclodextrin, and combinations thereof.

Any lubricants can be used without limitation insofar as they can be used for pharmaceutical products or food compositions. Examples of lubricants include calcium stearate, magnesium stearate, sodium stearyl fumarate, carnauba wax, starch, sucrose fatty acid ester, light anhydrous silicic acid, macrogol, talc, hydrogenated vegetable oil, and the like.

Any colorants and light shielding agents can be used without limitation, insofar as they can be used for pharmaceutical products or food compositions. Examples of colorants include powdered gambir tannin, turmeric extract, methylrosanilinium chloride, yellow iron oxide, yellow iron sesquioxide, OPASPRAY K-1-24904, orange essence, brown iron oxide, carbon black, caramel, carmine, carotene liquid, β-carotene, light sensitive element No. 201, licorice extract, gold leaf, Sasa albo-marginata extract, black iron oxide, light anhydrous silicic acid, Daemonorops draco (kekketsu), zinc oxide, titanium oxide, iron sesquioxide, disazo yellow, Food Blue No. 1 and its aluminum lake, Food Blue No. 2 and its aluminum lake, Food Yellow No. 4 and its aluminum lake, Food Yellow No. 5 and its aluminum lake, Food Green No. 3 and its aluminum lake, Food Red No. 2 and its aluminum lake, Food Red No. 3 and its aluminum lake, Food Red No. 102 and its aluminum lake, Food Red No. 104 and its aluminum lake, Food Red No. 105 and its aluminum lake, Food Red No. 106 and its aluminum lake, sodium hydroxide, talc, sodium copper chlorophyllin, copper chlorophyll, powdered hull-less barley green tea extract, hull-less barley green tea extract, phenol red, sodium fluorescein, d-borneol, malachite green, octyldodecyl myristate, methylene blue, medicinal carbon, riboflavin butyrate, riboflavin, powdered green tea, manganese ammonium phosphate, riboflavin sodium phosphate, rose oil, turmeric color, chlorophyll, carminic acid color, Food Red No. 40 and its aluminum lake, water-soluble annatto, sodium iron chlorophyllin, dunaliella carotene, paprika color, carrot carotene, potassium norbixin, sodium norbixin, palm oil carotene, beat red, grape pericarp color, black currant color, monascus color, safflower red color, safflower yellow color, marigold color, sodium riboflavin phosphate, madder color, alkanet color, aluminum, potato carotene, shrimp color, krill color, orange color, cacao color, cacao carbon black, oyster color, crab color, carob color, fish scale foil, silver, kusagi (Clerodendrum trichotomum) color, gardenia blue color, gardenia red color, gardenia yellow color, kooroo color, chlorophin, kaoliang color, bone carbon black, bamboo grass color, Shea nut color, lithospermum root color, red sandalwood color, vegetable carbon black, sappan color, spirulina color, onion color, tamarind color, corn color, tomato color, peanut color, phaffia color, pecan nut color, monascus yellow, powdered annatto, haematococcus algae color, purple sweet potato color, purple corn color, purple yam color, vegetable oil soot color, lac color, rutin, enju (Styphnolobium japonicum) extract, buckwheat whole-plant extract, logwood color, red cabbage color, red rice color, red radish color, adzuki bean color, Hydrangea serrata leaf extract, sepia color, uguisukagura (Lonicera gracilipes) color, elderberry color, olive tea, cowberry color, gooseberry color, cranberry color, salmon berry color, strawberry color, dark sweet cherry color, cherry color, thimbleberry color, deberry color, pineapple juice, huckleberry color, grape juice color, black currant color, blackberry color, plum color, blueberry color, berry juice, boysenberry color, whortleberry color, mulberry color, morello cherry color, raspberry color, red currant color, lemon juice, loganberry color, chlorella powder, cocoa, saffron color, beefsteak plant color, chicory color, layer color, hibiscus color, malt extract, paprika powder, red beet juice, carrot juice, and the like.

Examples of light shielding agents include titanium oxide, iron sesquioxide, yellow iron sesquioxide, black iron oxide, Food Blue No. 1 aluminium lake, Food Blue No. 2 aluminium lake, Food Yellow No. 4 aluminium lake, Food Yellow No. 5 aluminium lake, Food Green No. 3 aluminium lake, Food Red No. 2 aluminium lake, Food Red No. 3 aluminum lake, Food Red No. 102 aluminium lake, Food Red No. 104 aluminium lake, Food Red No. 105 aluminium lake, Food Red No. 106 aluminium lake, Red No. 40 aluminium lake, and the like.

Pharmaceutical hard capsules may contain titanium oxide as a light shielding agent to prevent degradation of content due to ultraviolet rays etc.

It is usually preferable that the capsule film after preparation contains a few percentage of residual moisture. When capsules after molding are dried in the range of 30° C. to 100° C., moisture content of the capsules settles to a specific saturated residual moisture level according to the solids content and composition of the capsules. Of course, when the drying treatment is performed at a higher temperature, the moisture content settles to a saturated moisture level in a shorter time. The residual moisture content depends on the environmental humidity during capsule storage, and changes almost reversibly. That is, the saturated moisture level after fully drying at 30 to 100° C., and further storage at a constant temperature and relative humidity for several days, settles to a constant level. In the present invention, the saturated moisture level after storage at room temperature and a relative humidity of 43% for several days is used.

Containing a small amount of residual moisture is rather preferable in order to maintain breakage resistance. The residual moisture content, as measured at room temperature and a relative humidity of 43% in terms of saturated moisture level, is preferably at least 1% or more, preferably 2% or more, and more preferably 3% or more, based on the total weight of the capsule film. On the other hand, an excessively large residual moisture content may cause a reaction with an encapsulated drug during long-term storage. Therefore, the residual moisture content is preferably 8% or less, and more preferably 6% or less.

The residual saturated moisture level can be expressed in terms of water content calculated from loss-on-drying, and can be measured in the following manner.

Method for Determining Water Content of Capsule Film by the Loss-On-Drying Method A sample (a hard capsule or a casted-film) is placed into a desiccator having an atmosphere in which the humidity is made constant by placing a saturated aqueous solution of potassium carbonate in the desiccator, and the desiccator is sealed. The sample is controlled in humidity at 25° C. for 1 week. In the presence of a saturated aqueous solution of potassium carbonate, an atmosphere with a relative humidity of approximately 43% can be created. The weight (wet weight) of the sample after the humidity control is measured. The sample is then heated at 105° C. for 2 hours, and the weight (dry weight) of the sample is measured again. From the difference between the weight of the sample before drying (wet weight) and the weight of the sample after drying (dry weight), the amount of water decreased by heating and drying at 105° C. for 2 hours (water content) is calculated according to the following formula.

$$\text{Water content (\%)} = [(\text{Wet weight of sample}) - (\text{Dry weight of sample})/\text{Wet weight of sample}] \times 100$$

(2) Method for Preparing Hard Capsule

The method for preparing a capsule-preparing solution (immersion liquid) is not particularly limited. Examples of methods include, but are not limited to, a method in which after optionally dissolving a gelling agent and/or a gelling aid in purified water heated to about 70 to 80° C., a water-soluble cellulose compound is dispersed in the purified water, and the dispersion is then cooled to a desired temperature of immersion liquid (usually 35 to 60° C., preferably 40 to 60° C.) to dissolve the water-soluble cellulose compound, thus preparing a uniform capsule-preparing solution (immersion liquid); and a method in which after a water-soluble cellulose compound is dispersed in hot water of about 70 to 80° C. and the dispersion is once cooled to dissolve the water-soluble cellulose compound, a gelling agent and/or a gelling aid is added to and dissolved in the solution as necessary, and the resulting solution is heated again to about 30 to 50° C. to prepare a uniform capsule-preparing solution (immersion liquid) and adjust the solution to a desired temperature of the immersion liquid. Further, examples of forming methods by thermal gelation described below include a method in which a water-soluble cellulose compound is dispersed in hot water of about 70 to 90° C. without adding a gelling agent or a gelling aid, and the resulting dispersion is once cooled to around room temperature or lower to dissolve the water-soluble cellulose compound.

The viscosity of the capsule-preparing solution is not particularly limited. Preferably, the viscosity of the capsule-preparing solution is generally 100 to 20,000 mPa·s, and more preferably 300 to 10,000 mPa·s, under the temperature conditions used for immersion of a capsule-forming pin (temperature of immersion liquid) (30 to 80° C., preferably 40 to 60° C.). The amount of solvent in the capsule-preparing solution may be, for example, typically 60 to 90 wt %, and preferably 70 to 85 wt %. The total amount of the hard capsule film components, excluding the solvent, in the capsule-preparing solution may be, for example, 10 to 40 wt %, and preferably 15 to 30 wt %.

The viscosity herein refers to a viscosity as measured with a Brookfield rotational viscometer at a predetermined temperature at 60 rpm for 1 minute using a No. 2 rotor for a viscosity of less than 500 mPa·s, a No. 3 rotor for a viscosity of at least 500 mPa·s and less than 2000 mPa·s, and a No. 4 rotor for a viscosity of 2000 mPa·s or more.

The concentration of each component contained in the capsule-preparing solution is described below.

The method for preparing (molding) a hard capsule is not particularly limited, as long as the capsule-preparing solution according to the present invention is used to prepare a capsule. A hard capsule is generally produced by immersing a mold pin, which is a mold for forming capsules, into an aqueous solution of a capsule film-forming material; then curing and drying the film adhered to the mold pin when the mold pin is drawn from the solution, to thereby obtain a capsule with a desired shape and thickness (the dipping method). Specifically, the method for preparing a hard capsule may comprise the steps of: preparing a capsule-preparing solution, for example, by producing a capsule-preparing solution by the above method, or purchasing a capsule-preparing solution; and dipping a capsule-forming pin into the capsule-preparing solution and then drawing the pin from the solution to allow the solution adhered to the capsule-forming pin to gel, followed by drying the gelled film at 20 to 80° C. to prepare a capsule. In some case, molding can also be performed by cooling to increase viscosity and drying, without performing a gelation step.

More specifically, the hard capsule used in the present invention can be produced through the following molding steps:

(1) a step of immersing a capsule-forming pin into a capsule-preparing solution (immersion liquid) containing a cellulose compound (and, if necessary, a gelling agent and/or a gelling aid) (dipping step);
(2) a step of withdrawing the capsule-forming pin from the capsule-preparing solution (immersion liquid) to allow the solution adhering to the outer surface of the capsule-forming pin to gel (gelation step);
(3) a step of drying the gelled capsule film (gelled film) formed on the outer surface of the capsule-forming pin (drying step); and
(4) a step of removing the dried capsule film from the capsule-forming pin (removal step).

If necessary, the following heating step may be performed after step (4):
(5) a step of heating the gelled capsule film (gelled film) to 30 to 150° C., which is performed after the gelation step (2) and which may be before, after, or simultaneously with the drying step (3) or after the removal step (4).

When a solution not containing a gelling agent, such as carrageenan, is used as a capsule-preparing solution (immersion liquid), the gelation step (2) can be performed by using a capsule-forming pin heated to 60° C. or higher, which utilizes the property such that a water-soluble cellulose compound itself becomes a gel at a temperature of 60° C. or more (thermal gelation method). Specifically, in the dipping step (1), a capsule-preparing solution (immersion liquid) adjusted to a constant temperature of 25 to 50° C., preferably 35 to 45° C., is prepared; and a capsule-forming pin, which is heated to an appropriate temperature of, for example, 60 to 150° C., preferably 60 to 120° C., and more preferably 70 to 90° C., according to the liquid temperature of the capsule-preparing solution, is immersed in the capsule-preparing solution. Subsequently, in the gelation step (2), the capsule-forming pin is drawn from the capsule-preparing solution (immersion liquid) to allow the capsule-preparing solution adhered to the outer surface of the capsule-forming pin to gel.

On the other hand, when a solution containing a gelling agent, such as carrageenan, is used as a capsule-preparing solution (immersion liquid), the gelation step (2) can be performed by adjusting the surrounding temperature of the capsule manufacturing apparatus to typically 35° C. or less, preferably 30° C. or less, and more preferably room temperature or lower, so as to allow the capsule-preparing solution adhered to the outer surface of the capsule-forming pin to cool (cold gelation method). This utilizes the property such that the solution becomes a gel at a temperature of 50° C. or lower. Specifically, cold gelation is performed as follows. In the dipping step (1), a capsule-preparing solution (immersion liquid) whose temperature is kept constant at 35 to 60° C., preferably 40 to 60° C., is prepared; and a capsule-forming pin, which is heated to an appropriate temperature of 10 to 30° C., preferably 13 to 28° C., and more preferably 15 to 25° C., according to the liquid temperature of the capsule-preparing solution, is dipped in the capsule-preparing solution. Subsequently, in the gelation step (2), the capsule-forming pin is drawn from the capsule-preparing solution (immersion liquid) to allow the capsule-preparing solution adhered to the outer surface of the capsule-forming pin to gel.

The drying step (3) can be performed at room temperature. The drying step (3) is usually performed by blowing room-temperature air. The removal step (4) is performed by detaching, from the capsule-forming pin, the dry capsule film formed on the surface of the capsule-molding pin.

The optional heating step (5) can be performed after the gelation step (2), that is, after the capsule-preparing solution becomes a gel (is solidified). The heating treatment may be performed at any stage after the gelation step (2); and can be performed, for example, before, after, or during the drying step (3), or after the removal step (4). Preferably, after the gelation step (2), the gelled capsule film is subjected to a drying step at room temperature, and a heating treatment is performed with the gelled capsule film being in a dried or semi-dried state. The heating temperature is not particularly limited, as long as it is within the range of 30 to 150° C. The heating temperature is preferably in the range of 40 to 100° C., and more preferably 50 to 80° C. The heating treatment can usually be performed by sending air of 30 to 150° C.

The capsule film thus prepared is cut to a predetermined length, and then provided as a hard capsule with a pair of a body portion and a cap portion being engaged or not engaged with each other.

The film thickness of hard capsules is usually in the range of 50 to 200 μm. In particular, the side wall thickness of currently commercially available capsules is typically 70 to 150 μm, and preferably 80 to 120 μm. The size of hard capsules includes Size No. 00, No. 0, No. 1, No. 2, No. 3, No. 4, No. 5, etc. In the present invention, any size of hard capsules can be used.

A solidification method that exclusively relies on moisture evaporation from a capsule-preparing solution and drying, without involving gelation phenomena, can also form a capsule film.

When hard capsules are molded using polyvinyl alcohol and a polyvinyl alcohol copolymer as base materials, these base materials themselves do not have thermal gelation properties. Therefore, a cold gelling agent is used, and dipping and drying can be performed in the same manner as the cold gelation method for cellulose compounds. However, it is preferable that the drying temperature is relatively high and in the range of 80 to 150° C. That is, only the drying conditions are preferably similar to those of the thermal gelation method described above.

(3) Filling of the Hard Capsule with Content, and Use of the Hard Capsule

The method of filling the hard capsule with content is not particularly limited.

Filling of the hard capsule with content can be performed, for example, by using a known capsule-filling machine disclosed in JP2007-144014A, JP2000-226097A, or the like, such as a fully automatic capsule-filling machine (model name: LIQFIL super 80/150, produced by Qualicaps Co., Ltd.), and a capsule-filing and sealing machine (model name: LIQFIL super FS, produced by Qualicaps Co., Ltd.).

In the filling method, provisional joining and true joining of hard capsules are secured by a lock mechanism as disclosed in U.S. Pat. Nos. 3,508,678, 3,823,843, 4,040,536, 4,822,618, 5,769,267, etc. The hardness of the hard capsule is also important to stably maintain such a lock mechanism.

In order to prevent malicious opening and foreign matter entry, and to securely prevent leaks of liquid filling materials by more secure sealing in addition to the above-described lock mechanism by rubbing the cap and the body together, the capsule fitting portion may be sealed by using the band seal disclosed in JP2005-187412A or JP2009-504630A.

The use of the hard capsule of the present invention is not particularly limited. Preferable examples of uses include oral preparations, inhalation preparations, and the like.

It is preferable that oral preparations are promptly dissolved in the stomach or intestines. In order to allow a capsule film to be dissolved in the intestines and release a drug in the intestines, enteric capsules may also be famed by coating the capsule film surface with an enteric base material. Enteric capsules may also be formed by making a capsule film itself exclusively or partially using an enteric base material. The enteric capsule is not particularly limited as long as it has a property of not being dissolved in the stomach, but being dissolved in the intestines. For example, the enteric capsules may be capsules that are hardly dissolved in a dilute hydrochloric acid solution of pH 1.2 (Japanese Pharmacopoeia, first fluid) for more than 2 hours, and that are dissolved in a buffer solution of pH 6.8 (Japanese Pharmacopoeia, second fluid).

Further, a drug can be released from the hard capsule in a sustained manner. For gradual sustained release of a drug, the capsule film surface may be coated with a sustained-release film.

Inhalation preparations can be produced by sealing a single dose of a drug in each hard capsule and placing the capsule in a device, such as those disclosed in U.S. Pat. Nos. 4,069,819, 4,210,140, 7,669,596, U.S. Patent No. 2010-0300440A, etc. The capsule is pierced with a small pin, or broken to enable inhalation of the drug inside at an appropriate flow rate.

The content encapsulated in the hard capsule is not particularly limited. Examples include, but are not limited to, pharmaceutical products for humans and animals, quasi-drugs, cosmetics, and foods.

The form of the content is also not particularly limited. For example, the content may be in the form of a liquid, gel, powder, granules, tablets, pellets, or a mixture thereof (a hybridized state).

When the content encapsulated in the hard capsule is a pharmaceutical product, examples thereof include at least one kind of pharmaceutical ingredient selected from nourishment tonics, antipyretic/analgesic/anti-inflammatory drugs, psychotropic drugs, anti-anxiety drugs, antidepressant drugs, hypnotic/sedative drugs, antispasmodic drugs, drugs acting on the central nervous system, cerebral metabolism improvers, cerebral circulation improvers, antiepileptic drugs, sympathetic nerve stimulants, digestives, antacids, antiulcer drugs, antitussive/expectorant drugs, antiemetic drugs, respiration promoters, bronchodilators, antiallergic drugs, drugs for dentistry and oral cavity, antihistaminic drugs, cardiotonic drugs, antiarrhythmic drugs, diuretic drugs, antihypertensive drugs, vasoconstrictors, coronary vasodilators, peripheral vasodilators, antihyperlipidemic drugs, cholagogues, antibiotics, chemotherapeutic drugs, antidiabetic drugs, antiosteoporotic drugs, antirheumatic drugs, skeletal muscle relaxants, spasmolytic drugs, hormone preparations, alkaloid narcotics, sulfa drugs, anti-gout drugs, anticoagulant drugs, antineoplastic drugs, and the like. Such pharmaceutical ingredients are not particularly limited, and can be selected, for example, from a wide variety of known pharmaceutical ingredients. Specific examples include the ingredients described in paragraphs [0055] to [0060] of WO2006/070578.

When the content encapsulated in the hard capsule is a food, examples include, but are not limited to, functional ingredients, such as docosahexaenoic acid, eicosapentaenoic acid, α-lipoic acid, royal jelly, isoflavone, agaricus, acerola, aloe, aloe vera, turmeric, L-carnitine, oligosaccharide, cacao, catechin, capsaicin, chamomile, agar, tocopherol, linolenic acid, xylitol, chitosan, GABA, citric acid, chlorella, glucosamine, ginseng, coenzyme Q10, brown sugar, collagen, chondroitin, bracket fungus, squalene, stevia, ceramide, taurine, saponin, lecithin, dextrin, *Houttuynia cordata*, niacin, *Bacillus* natto, bittern, lactic acid bacteria, saw palmetto, honey, *Coix lacryma-jobi* var. *ma-yuen*, Japanese apricot (ume) extract, pantothenic acid, hyaluronic acid, vitamin A, vitamin K, vitamin C, vitamin D, vitamin B1, vitamin B2, vitamin B6, vitamin B12, quercetin, protein, propolis, mulukhiya, folic acid, lycopene, linoleic acid, rutin, and *Ganoderma lucidum*.

(4) Evaluation of Hardness

The hardness of the hard capsule can be evaluated, for example, by preparing the capsule-preparing solution described above, then forming a casted-film by using a film applicator, and evaluating hardness of the casted-film. The casted-film formed has a thickness of 100 µm±5 µm, and is cut into a size of 10 mm×50 mm. The casted-film is then controlled in humidity at 25° C. and a relative humidity of 43% (a saturated aqueous solution of potassium carbonate), for example, for 1 week, and the hardness of the casted-film is then evaluated in a compression test.

Figure 2A:
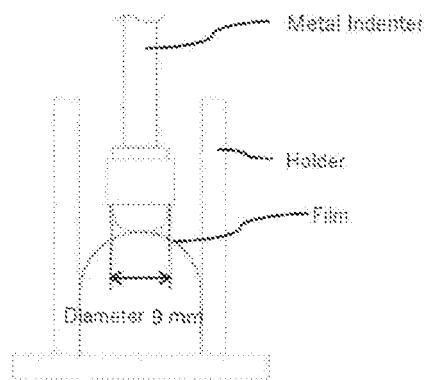
FIG. 2(a) shows a state before compression.
Figure 2B:
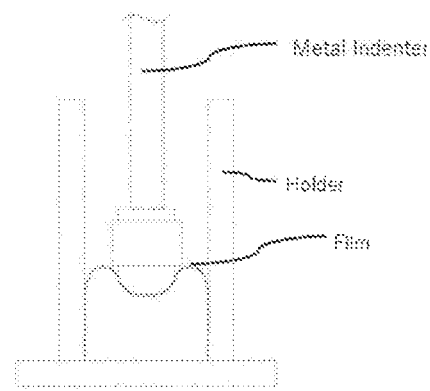
FIG. 2(b) shows a state after compression.
Figure 2C:
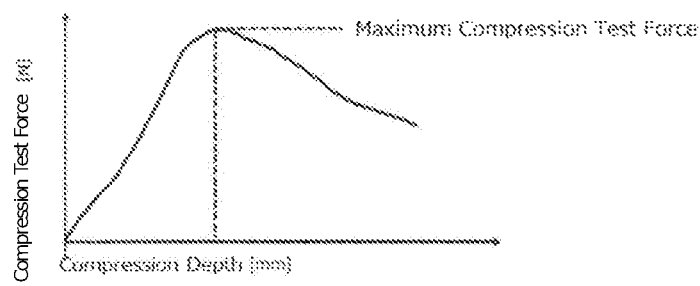
FIG. 2(c) shows a relationship between compression depth and compression test force. The diameter of the indenter is 9 mm.

The hardness evaluation is performed in the following manner. The moisture-controlled casted-film curved into an arch shape is set in the holder of an autograph (for example, AGS-J: Shimadzu Corporation) (as shown in FIG. 1a, the film set in the holder had a width of 2 cm and a height of 2 cm). 5- to 8-mm film top is compressed with a metal indenter (FIG. 2b), and the peak of the compression test force value of the casted-film is determined (FIG. 2c). The obtained value is compared with the value of the compression test force of a reference standard (a film produced using the same components as those of the test specimen except for the hardness improving agent, and containing the base in an amount increased by an amount corresponding to the amount of the hardness improving agent), thereby evaluating the hardness. The compression speed is, for example, 50 ram/min, and the diameter of the metallic indenter is, for example, 9 mm (FIG. 2b).

Figure 3A:
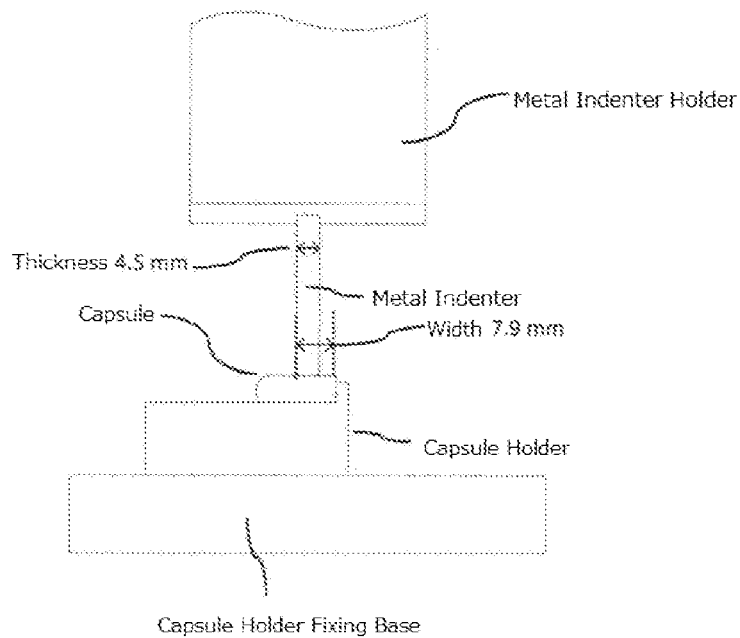
FIG. 3(a) shows the positions of the indenter, the capsule, and the capsule holder upon compression of the capsule. The width of the indenter is 4.5 mm. The capsule compression position is 7.9 mm from the cut end of the capsule.
Figure 3B:
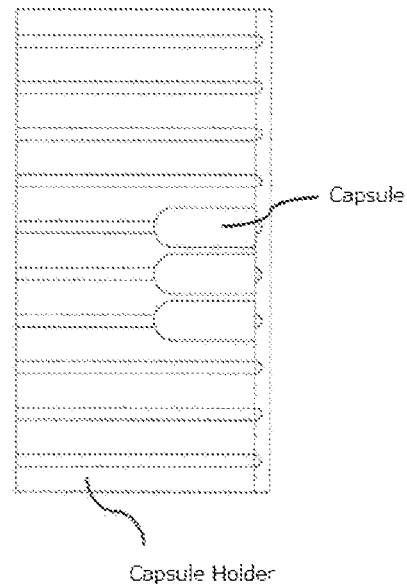
FIG. 3(b) is an upper view of a capsule set in a capsule holder.

The hardness of the capsule is evaluated in the following manner. The body portion of the moisture-controlled capsule is set in an autograph (for example, AGS-J: Shimadzu Corporation) (FIGS. 3a and 3b), and compressed with a metal indenter (FIG. 3a), thereby determining the compression test force value at a compression depth freely selected. The compression speed is, for example, 10 ram/min, and the compression depth is, for example, 3 mm (FIG. 3a). The compression with a metal indenter is performed on a portion of the capsule from 3.4 to 7.9 mm from the cut end of the capsule.

The hardness can be evaluated, for example, according to the following criteria, with the compression test force of the reference standard not containing the hardness improving agent described below being defined as 100.

A compression test force of 110 or more and less than 120 is assessed as "improved hardness."

A compression test force of 120 or more is assessed as "highly improved hardness."

A compression test force of 90 or more and less than 110 is assessed as "unchanged hardness."

A compression test force of less than 90 is assessed as "weakening."

2. Hard Capsule Comprising Starch Decomposition Product, and Solution for Preparing the Hard Capsule (1) Hard Capsule The hard capsule according to this embodiment comprises a film containing a base, and a starch decomposition product as a hardness improving agent. The "hardness improving agent" as referred to in this section is distinguished from the hardness improving agent used in subsequent section 3. The base is at least one member selected from the group consisting of cellulose compounds, polyvinyl alcohol, and polyvinyl alcohol copolymers. Preferably, the base is at least one member selected from the group consisting of hydroxypropylmethylcellulose, polyvinyl alcohol, and polyvinyl alcohol copolymers. The amount of base in this embodiment is obtained by subtracting the total weight % of the capsule film components other than the base from 100 wt %, when the total amount of the hard capsule film components, excluding moisture, is defined as 100 wt %.

"Starch decomposition product" is a generic term for intermediate products obtained during the process of decomposing starch into dextrose, and is represented by $(C_6H_{10}O_5)_n \cdot xH_2O$. The starch decomposition product can be obtained by treating starch with oxygen, acid, heat, etc., in accordance with a known method for producing dextrin. The starch decomposition product includes dextrin and maltose.

"Dextrin" is a generic term for intermediate products obtained during the process of decomposing starch into maltose or dextrose (the Japanese Pharmacopoeia, 16th edition). Dextrin is obtained by treating starch with oxygen, acid, heat, etc., and is represented by $(C_6H_{10}O_5)_n \cdot xH_2O$. Dextrin is roughly classified as shown below in Table 2.

TABLE 2

| Name | Iodine reaction | Specific optical rotation | Molecular weight |
|---|---|---|---|
| Amylodextrin | Indigo blue | +190 to +195° | >10,000 |
| Erythrodextrin | Red to brown | +194 to +196° | 6,200 to 7,000 |
| Achrodextrin | Pale brown | +192° | 3,700 |
| Maltodextrin | Colorless | +181 to +183° | — |

Examples of commercially available dextrin include the Martrin(Registered Trademark) series of GPC, the Glucidex (Registered Trademark) series of Roquette, the Amycol (Trademark) series and the JP Dextrin(Trademark) series of Nippon Starch Chemical Co., Ltd., the Pinedex(Trademark) series of Matsutani Chemical Industry Co., Ltd., and the like.

DE is an abbreviation for Dextrose Equivalent, a common expression in the art for describing the total reducing sugar content of a material, expressed as percent dextrose on a dry weight basis. Reducing sugar is measured as glucose and calculated in terms of a ratio of the reducing sugar to the total solids content, and is an index showing the degree of decomposition of a decomposition product. The measurement of DE value is generally performed according to the Somogyi method, but is not limited thereto. This method is superior to the molecular weight distribution measurement itself in terms of reproducibility of the obtained value. The starch decomposition product with a DE value of 10 or less may be called dextrin. The starch decomposition product with a DE value of more than 10 and less than 20 may be called maltodextrin. The starch decomposition products with a DE value of more than 20 may be called powder candy.

Generally commercially available dextrin is a mixture of starch decomposition products having different degrees of polymerization and having distribution peaks corresponding to the molecular weight of glucose polymers constituting the dextrin. In this case, the DE value of the dextrin is in accordance with the indication of the product. The DP value represented by the formula

*DP* value=100/*DE* value refers to the degree of polymerization of glucose per dextrin molecule, that is, the average number of glucose units in dextrin.

The calculated DE value refers to an apparent DE value when dextrin comprises two or more kinds of starch decomposition product having different DE values. The calculated DE value is determined as follows. First, for each starch decomposition product combined, a value calculated from [DE value of the starch decomposition product×amount of the starch decomposition product added (wt %)] is obtained. The sum of the thus-obtained values of the starch decomposition products combined is calculated. This sum is divided by the total amount of the starch decomposition products added (wt %) to obtain a calculated DE value. The amount of the starch decomposition products added is their content, based on 100 wt % of the total hard capsule film components, excluding moisture.

For example, when the hard capsule comprises a starch decomposition product A with a DE value of DEa in an amount of Wa wt %, and a starch decomposition product B with a DE value of DEb in an amount of Wb wt %, the calculated DE value is represented by the following formula.

Calculated $DE$ value=$\{(DEa \times Wa)+(DEb \times Wb)\}/(Wa+Wb)$

In this embodiment, a starch decomposition product with a DE value of more than 11 can be used as the starch decomposition product. A starch decomposition product with a DE value of less than 40 can be used as the starch decomposition product. Alternatively, the starch decomposition product used can be two or more kinds of starch decomposition product combined to have a calculated DE value of more than 11 and less than 40 (provided that the two or more kinds of starch decomposition product exclude starch decomposition products solely having a DE value of 5 or less and monosaccharides). The lower limit of the DE value of the starch decomposition product with a DE value of more than 11 and less than 40 is preferably 13. The upper limit of the DE value of the starch decomposition product with a DE value of more than 11 and less than 40 is preferably 38, and more preferably 33. When the hardness improving agent is at least one member selected from the group consisting of two or more kinds of starch decomposition product combined to have a calculated DE value of more than 11 and less than 40, the two or more kinds of starch decomposition product are preferably selected from starch decomposition products having a DE value of more than 5 and not more than 50. More preferably, the lower limit of the DE value of at least one of the starch decomposition products contained in the two or more kinds of starch decomposition product is 6. The upper limit of the DE value of at least one of the starch decomposition products contained in the two or more kinds of starch decomposition product is preferably 40, and more preferably 38. Specifically, the two or more kinds of starch decomposition product are preferably a combination of a starch decomposition product with a DE value of more than 5 and not more than 11, and a starch decomposition product with a DE value of at least 40 and not more than 50. When the amount of starch decomposition product solely having a DE value of more than 5 and not more than 11 is Wa wt %, and the amount of starch decomposition product solely having a DE value of at least 40 and not more than 50 is Wb wt %, the ratio of Wb/(Wa+Wb) is preferably 0.5 or less, and more preferably 0.3 or less.

The lower limit of the total amount of the hardness improving agent in this embodiment is 3 wt %, preferably 5 wt %, and more preferably 10 wt %, based on 100 wt % of the total hard capsule film components, excluding moisture. The upper limit of the total amount of the hardness improving agent in this embodiment is 50 wt %, preferably 30 wt %, and more preferably 20 wt %, based on 100 wt % of the total hard capsule film components, excluding moisture.

When a monosaccharide with a DE value of 100 (glucose) is mixed with a starch (glucose units: several thousands to several tens of thousands or more) with a DE value of nearly 0, such as starch, so as to achieve a calculated DE value within the above-mentioned range, no capsule film hardness improving effects can be obtained.

In this embodiment, when hydroxypropylmethylcellulose is used as a base, a disaccharide with a DE value of 50 may be added in order to improve dissolution of the hard capsule (JP2010-270039A). However, particularly when a large amount of monosaccharide or disaccharide is added, the resulting capsule film becomes brittle. Therefore, it is preferable that the amount of monosaccharide and/or disaccharide be in the range of 10 wt % or less, based on 100 wt % of the total hard capsule film components, excluding moisture, and be smaller than the amount of the hardness improving agent in this embodiment.

The hard capsule in this embodiment may further comprise at least one clay mineral selected from the group consisting of talc, bentonite, and kaolin. Examples of bentonite, talc, and kaolin that can be used include those disclosed in the subsequent section 3. Incorporating a clay mineral into the hard capsule can further enhance the hardness of the capsule.

When a hardness improving agent and the clay mineral are used in combination, the total amount of the hardness improving agent and clay mineral contained can be set within the range of at least 4 wt % and not more than 50 wt %, based on 100 wt % of the total hard capsule film components, excluding moisture. The lower limit of this range is preferably 13 wt %, and more preferably 18 wt %. The upper limit of this range is preferably 80 wt %, and more preferably 70 wt %, even more preferably 50 wt %, and still even more preferably 35 wt %. This range can be appropriately set according to the sum of the amount of the hardness improving agent and the amount of clay mineral described below in the subsequent section 3. More specifically, when the clay mineral is talc, the amount of hardness improving agent is preferably in the range of at least 10 wt % and not more than 30 wt %, and the amount of talc is preferably in the range of more than 10 wt % and not more than 40 wt %. When the clay mineral is bentonite, the amount of hardness improving agent is preferably in the range of at least 10 wt % and not more than 30 wt %, and the amount of bentonite is preferably in the range of at least 1 wt % and not more than 8 wt %. When the clay mineral is kaolin, the amount of hardness improving agent is preferably in the range of at least 10 wt % and not more than 30 wt %, and the amount of kaolin is preferably in the range of at least 11 wt % and not more than 50 wt %.

Specific examples of the composition of the hard capsule are as follows: when the amount of hard capsule film components, excluding moisture, is defined as 100 wt %, the amount of hardness improving agent is as described above; and the amount of base can be the remainder of the total content of the hard capsule film components, excluding moisture, based on 100 wt % of the total hard capsule film components, excluding moisture. Specifically, the amount of base is 20 to 97 wt %, preferably 50 to 93 wt %, more preferably 65 to 90 wt %, and even more preferably 70 to 85 wt %. When the hard capsule film comprises component(s)

other than the base and the hardness improving agent, the amount of gelling agent is 0.025 to 2.5 wt %, preferably 0.05 to 2.3 wt %, more preferably 0.075 to 2 wt %, and even more preferably 0.1 to 1.8 wt %. When the hard capsule film comprises a gelling aid, such as potassium chloride, the amount of gelling aid is, for example, 2.5 wt % or less, preferably 0.1 to 2.3 wt %, more preferably 0.15% to 2 wt %, and even more preferably 0.2 to 1.8 wt %. When the hard capsulec film of in this embodiment comprises a plasticizer, the amount of plasticizer is usually, for example, within the range of 15 wt % or less, preferably 13 wt % or less, more preferably 11 wt % or less, and even more preferably 8 wt % or less. Similarly, when the hard capsule film comprises a lubricant, a colorant, a light shielding agent, a sequestrant, a flavoring agent, or the like, the amount of each additive can be suitably set within the range of 15 wt % or less, preferably 13 wt % or less, more preferably 11 wt % or less, and even more preferably 8 wt % or less.

(2) Hard Capsule-Preparing Solution

The capsule-preparing solution for forming the hard capsule according to this embodiment comprises a solvent and components described above in section 2. (1). The solvent is not particularly limited, as long as it is an aqueous solvent. The solvent is preferably water, ethanol, or a mixture thereof, and is more preferably water.

The concentrations of the above components contained in the hard capsule-preparing solution are not limited, as long as the amounts of the components in the hard capsule after preparation are as described above. More specifically, when the total amount of the components of the preparation solution, excluding moisture, is defined as 100 wt %, the concentrations of the components in the capsule-preparing solution are not limited as long as the amounts of the components in the hard capsule after preparation become the above-mentioned contents in the hard capsule. The final concentrations in the capsule-preparing solution may be, for example, the following concentrations. The final concentration refers to the concentration in the final solution, that is, the concentration in the solution actually used to prepare the capsule.

The concentration of the base is 10 to 30 wt %, preferably 12 to 20 wt %, and more preferably 14 to 18 wt %; the concentration of the hardness improving agent is 0.6 to 10 wt %, preferably 1 to 6 wt %, and more preferably 2 to 4 wt %. When the capsule-preparing solution comprises component(s) other than the base and the hardness improving agent, the concentration of the gelling agent is 0.005 to 0.5 wt %, preferably 0.01 to 0.45 wt %, and more preferably 0.015 to 0.4 wt %. When a gelling aid is used, the concentration of the gelling aid is 0.5 wt % or less, 0.02 to 0.5 wt %, preferably 0.03 to 0.40 wt %, and more preferably 0.04 to 0.35 wt %. When the capsule-preparing solution contains a lubricant, a colorant, a light shielding agent, a sequestrant, a flavoring agent, and the like, the amount of each of such additives can be set within the range of not more than 0.5 wt %.

When the capsule-preparing solution according to this embodiment further contains at least one clay mineral selected from the group consisting of talc, bentonite, and kaolin, the amount of clay mineral may be, for example, 0.2 to 10 wt %, and preferably 0.5 to 4 wt %, in terms of the final concentration in the capsule-preparing solution.

The method for preparing the capsule-preparing solution is as described above in the section "1. Explanation of Terms."

(3) Method for Preparing Hard Capsule

The method for preparing a hard capsule is as described above in the section "1. Explanation of Terms." The method for preparing a hard capsule in this embodiment is also a method for improving the hardness of a hard capsule.

3. Hard Capsule Comprising at Least One Mineral Clay Mineral Selected from the Group Consisting of Talc, Bentonite, and Kaolin, and Solution for Preparing the Hard Capsule (1) Hard Capsule The hard capsule in this embodiment comprises a film comprising a base and at least one clay mineral selected from the group consisting of talc, bentonite, and kaolin as a hardness improving agent. The "hardness improving agent" as referred to in this section can be distinguished from the hardness improving agent used in the preceding section 2. The base is at least one member selected from the group consisting of cellulose compounds, polyvinyl alcohol, and polyvinyl alcohol copolymers, and preferably at least one member selected from the group consisting of hydroxypropylmethylcellulose, polyvinyl alcohol, and polyvinyl alcohol copolymers. The amount of base in this embodiment is obtained by subtracting the total weight % of the capsule film components other than the base from 100 wt %, when the total amount of the hard capsule film components, excluding moisture, is defined as 100 wt %.

In this embodiment, talc is a natural hydrous magnesium silicate, and is also called soapstone. Pure talc is $Mg_3Si_4O_{10}(OH)_2$ (molecular weight: 379.27). Talc comprises $Mg_3Si_4O_{10}(OH)_2$ as a main component, and may also comprise chlorite (hydrous magnesium aluminum silicate), magnesite (magnesium carbonate), calcite (calcium carbonate), and dolomite (calcium carbonate magnesium). Talc does not comprise asbestos.

The particle size of talc as measured by the laser diffraction-scattering method (JIS Z 8825:2013) is about 0.5 to 30 μm, and preferably about 3.0 to 15.0 μm. The apparent density (JIS Z 2504:2012) of talc is 0.12 to 0.40 g/cm$^3$, and preferably 0.15 to 0.35 g/cm$^3$. The specific surface area of talc as determined by the BET method (JIS Z 8830:2013) is about 2.5 to 40 m$^2$/g, and preferably about 5 to 20 m$^2$/g.

Examples of commercially available talc include Rose Talc, Micro Ace P-4, Micro Ace P-3, Micro Ace P-2, SG-95, and MS-KY (Nippon Talc Co., Ltd.); Talc Powder CT-250, Talc Powder CT-35 and Talc Powder EX-15 (Yamaguchi Mica Co., Ltd.); TALC JA-13R, TALC JA-24R, TALC JA-46R, TALC JA-68R, TALC JA-80R, TALC MMR, TAL-CSW-A, and TALC SW-Special (Asada Milling Co., Ltd.); IMP 1886L Talc BC (Ina Trading Co., Ltd.); Luzenac Pharma (GSI Creos Corp.); and the like.

In this embodiment, bentonite is a natural special colloidal clay, and is a colloidal hydrous aluminum silicate. Bentonite comprises montmorillonite as a main component, which accounts for about 90% of bentonite. Bentonite feldspar, calcium sulfate, beidellite, calcium carbonate, quartz, mica, manganese carbonate, etc., are said to account for the remaining 10%.

Examples of commercially available bentonite include Veegum F, Veegum HV, and Veegum R (R.T. Vanderbilt C. Inc., USA); Kunipia G, Kunipia F (produced by Kunimine Industries Co., Ltd.); Bentolite (Wilbur-Ellis); Bentonite TONEJIRUSHI (Kanben Mining Co., Ltd.); Bengel FW and Bengel (Nihon Yuukinendo Co., Ltd.); Polargel NF (Volclay Japan Co., Ltd.); and the like.

In this embodiment, kaolin corresponds to natural hydrous aluminum silicate represented by $Al_2O_3/2SiO_2/2H_2O$.

Examples of commercially available kaolin include 2747 Kaolin USP BC (Ina Trading Co., Ltd.), RF Amazonian White Clay (DKSH Japan K.K.), White Clay and Red Clay (Matsumoto Trading Co., Ltd.), and the like.

When the hard capsule contains talc as a hardness improving agent, the lower limit of talc content in this embodiment is more than 10 wt %, preferably 10.5 wt %, and more preferably 11 wt %, based on 100 wt % of the total hard capsule film components, excluding moisture. The upper limit of talc content is 50 wt %, and preferably 40 wt %, based on 100 wt % of the total hard capsule film components, excluding moisture.

A more specific example of the composition of the hard capsule containing talc as a hardness improving agent is that when the total amount of the hard capsule film components, excluding moisture, is defined as 100 wt %, the talc content is as described above; and the amount of base can be the remainder of the total content of the capsule film components excluding moisture, based on 100 wt % of the total hard capsule film components, excluding moisture. Specifically, the amount of base is 45 to 90 wt %, preferably 55 to 85 wt %, and more preferably 65 to 80 wt %. When the hard capsule comprises components other than the base and the hardness improving agent, the amount of gelling agent may be, for example, 0.025 to 2.5 wt %, preferably 0.05 to 2.3 wt %, more preferably 0.075 to 2 wt %, and even more preferably 0.1 to 1.8 wt %, and the amount of base is 45 to 90 wt %, preferably 55 to 85 wt %, and more preferably 65 to 80 wt %. When the hard capsule further comprises a gelling aid, such as potassium chloride, its content may be, for example, in the range of 2.5 wt % or less, preferably 0.1 to 2.3 wt %, more preferably 0.15% to 2 wt %, and even more preferably 0.2 to 1.8 wt %.

When the capsule film of the hard capsule in this embodiment comprises a plasticizer, its content may be typically, for example, in the range of 15 wt % or less, preferably 13 wt % or less, more preferably 11 wt % or less, and even more preferably 8 wt % or less. Similarly, when the capsule film of the hard capsule comprises a lubricant, a colorant, a light shielding agent, a sequestrant, a flavoring agent, etc., the amount of each of such additives can be appropriately set within the range of 15 wt % or less, preferably 13 wt % or less, more preferably 11 wt % or less, and even more preferably 8 wt % or less.

When the capsule film of the hard capsule comprises bentonite as a hardness improving agent, the lower limit of bentonite content in this embodiment is more than 0.5 wt %, preferably 0.75 wt %, and more preferably 1 wt %, based on 100 wt % of the total hard capsule film components, excluding moisture. The upper limit of the bentonite content in this embodiment is less than 10 wt %, and preferably 8 wt %, based on 100 wt % of the total hard capsule film components, excluding moisture.

A more specific example of the composition of the hard capsule comprising bentonite as a hardness improving agent is that when the total amount of the hard capsule film components, excluding moisture, is defined as 100 wt %, the bentonite content is as described above, and the amount of base can be the remainder of the total content of the hard capsule film components, excluding moisture, based on 100 wt % of the total hard capsule film components, excluding moisture. Specifically, the amount of base is 45 to 99.9 wt %, preferably 55 to 99 wt %, more preferably 60 to 95 wt %, and even more preferably 65 to 90 wt %. When the hard capsule film comprises components other than the base and the hardness improving agent, the amount of gelling agent may be, for example, 0.025 to 2.5 wt %, preferably 0.05 to 2.3 wt %, more preferably 0.075 to 2 wt %, and even more preferably 0.1 to 1.8 wt %. When the hard capsule film further comprises a gelling aid, such as potassium chloride, its content may be, for example, in the range of 2.5 wt % or less, preferably 0.1 to 2.3 wt %, more preferably 0.15% to 2 wt %, and even more preferably 0.2 to 1.8 wt %. Further, when the hard capsule film in this embodiment comprises a plasticizer, the amount of plasticizer may be typically, for example, in the range of 15 wt % or less, preferably 13 wt % or less, more preferably 11 wt % or less, and even more preferably 8 wt % or less. Further, when the capsule film comprises a lubricant, a colorant, a light shielding agent, a sequestrant, a flavoring agent, etc., the amount of each of such additives can be appropriately set within the range of 15 wt % or less, preferably 13 wt % or less, more preferably 11 wt % or less, and even more preferably 8 wt % or less.

When the hard capsule film comprises kaolin as a hardness improving agent, the lower limit of the amount of hardness improving agent in this embodiment is 10 wt %, and preferably 15 wt %, based on 100 wt % of the total hard capsule film components, excluding moisture. The upper limit of the amount of the hardness improving agent in this embodiment is 50 wt %, preferably 40 wt %, and more preferably 30 wt %, based on 100 wt % of the total hard capsule film components, excluding moisture.

A more specific composition of the hard capsule comprising kaolin as a hardness improving agent is that when the total amount of the hard capsule film components, excluding moisture, is defined as 100 wt %, the amount of kaolin is as described above, and the amount of base can be the remainder of the total content of the components, excluding moisture, based on 100 wt % of the total hard capsule film components, excluding moisture. Specifically, the amount of base may be, for example, 65 to 90 wt %, preferably 70 to 85 wt %, and more preferably 75 to 80 wt %. When the hard capsule film comprises components other than the base and the hardness improving agent, the amount of gelling agent may be, for example, 0.025 to 2.5 wt %, preferably 0.05 to 2.3 wt %, more preferably 0.075 to 2 wt %, and even more preferably 0.1 to 1.8 wt %. When the hard capsule film further comprises a gelling aid, such as potassium chloride, the amount of gelling aid may be, for example, in the range of 2.5 wt % or less, preferably 0.1 to 2.3 wt %, more preferably 0.15% to 2 wt %, and even more preferably 0.2 to 1.8 wt %. Further, when the hard capsule film of the hard capsule in this embodiment comprises a plasticizer, the amount of plasticizer may be, for example, typically in the range of 15 wt % or less, preferably 13 wt % or less, more preferably 11 wt % or less, and even more preferably 8 wt % or less. Similarly, when the hard capsule film comprises a lubricant, colorant, a light shielding agent, a sequestrant, a flavoring agent, etc., the amount of each of such additives can be appropriately set within the range of 15 wt % or less, preferably 13 wt % or less, more preferably 11 wt % or less, and even more preferably 8 wt % or less.

Bentonite, talc, and kaolin may be used in a combination of two or three kinds. When two or three kinds of such clay minerals are used in combination, the lower limit of the total clay mineral content of the hard capsule can be the lowest value among the lower limits of the contents of the clay minerals used in combination. When two or more kinds of clay minerals are used in combination, the upper limit of the total clay mineral content of the hard capsule can be the highest value among the upper limits of the contents of the clay minerals used in combination.

Talc, bentonite, and kaolin are clay minerals that have a specific crystal structure and a layered structure. When a general inorganic filler (e.g., metal oxide) not having such a structure is added, the hardness improving effect of the present invention cannot be achieved.

(2) Hard Capsule-Preparing Solution

The capsule-preparing solution for forming the hard capsule according to this embodiment comprises a solvent and the components described above in section 3. (1). The solvent is not particularly limited, as long as it is an aqueous solvent. The solvent is preferably water, ethanol, or a mixture thereof; and water is more preferable.

The concentrations of the above components contained in the hard capsule-preparing solution are not limited, as long as the amounts of the components in the hard capsule after preparation become their contents of the hard capsule described above. That is, when the total amount of the components, excluding the solvent, in the capsule-preparing solution is defined as 100 wt %, the concentration of each component in the capsule-preparing solution is not limited, as long as the amount of each component in the hard capsule after preparation becomes its content of the hard capsule described above. For example, the following concentrations can be used as final concentrations in the capsule-preparing solution. The "final concentration" refers to a concentration in the final solution, that is, a concentration in the solution actually used to prepare the capsule.

The composition of the capsule-preparing solution may be, for example, as follows. When the hardness improving agent is talc, the amount of base is 9 to 18 wt %, preferably 11 to 17 wt %, and more preferably 13 to 16 wt %; and the amount of talc is 2 to 10 wt %, and preferably 2.2 to 8 wt %. When the capsule-preparing solution contains components other than the base and the hardness improving agent, the amount of gelling agent may be, for example, 0.005 to 0.5 wt %, preferably 0.01 to 0.45 wt %, and more preferably 0.015 to 0.4 wt %. When a gelling aid is used, its concentration may be, for example, 0.5 wt % or less, 0.02 to 0.5 wt %, preferably 0.03 to 0.40 wt %, and more preferably 0.04 to 0.35 wt %. When the capsule-preparing solution contains a lubricant, colorant, a light shielding agent, a sequestrant, a flavoring agent, etc., the amount of each of such additives can be appropriately set within the range of 0.5 wt % or less.

When the hardness improving agent is bentonite, the amount of base is 9 to 20 wt %, preferably 11 to 19.5 wt %, more preferably 12 to 19 wt %, and even more preferably 13 to 18 wt %; and the amount of bentonite is 0.02 to 10 wt %, and preferably 0.2 to 6 wt %. When the capsule-preparing solution contains components other than the base and the hardness improving agent, the amount of gelling agent may be, for example, 0.005 to 0.5 wt %, preferably 0.01 to 0.45 wt %, and more preferably 0.015 to 0.4 wt %. When a gelling aid is used, its concentration may be, for example, 0.5 wt % or less, 0.02 to 0.5 wt %, preferably 0.03 to 0.40 wt %, and more preferably 0.04 to 0.35 wt %. When the capsule-preparing solution contains a lubricant, colorant, a light shielding agent, a sequestrant, a flavoring agent, etc., the amount of each of such additives can be appropriately set within the range of 0.5 wt % or less.

When the hardness improving agent is kaolin, the amount of base is 13 to 18 wt %, preferably 14 to 17 wt %, and more preferably 15 to 16 wt %; and the amount of kaolin is 2 to 6 wt %, and preferably 3 to 4 wt %. When the capsule-preparing solution contains components other than the base and the hardness improving agent, the amount of gelling agent may be, for example, 0.005 to 0.5 wt %, preferably 0.01 to 0.45 wt %, and more preferably 0.015 to 0.4 wt %. When a gelling aid is used, its concentration may be, for example, 0.5 wt % or less, 0.02 to 0.5 wt %, preferably 0.03 to 0.40 wt %, and more preferably 0.04 to 0.35 wt %. When the capsule-preparing solution contains a lubricant, colorant, a light shielding agent, a sequestrant, a flavoring agent, etc., the amount of each of such additives can be appropriately set within the range of 0.5 wt % or less.

When bentonite, talc, and kaolin are used in a combination of two or more kinds, the lower limit of the total clay mineral content of the hard capsule can be the lowest value among the lower limits of the contents of the clay minerals used in combination and the upper limit of the total clay mineral content of the hard capsule can be the highest value among the upper limits of the contents of the clay minerals used in combination.

The method for preparing the capsule-preparing solution is as described above in the section "1. Explanation of Terms."

(3) Method for Preparing Hard Capsule

The method for preparing a hard capsule is as described above in the section "1. Explanation of Terms." The method for preparing a hard capsule in this embodiment is also a method of improving the hardness of a hard capsule.

EXAMPLES

The present invention is more specifically explained below in reference to Examples. However, the present invention is not limited to the Examples.

1. Test Example 1: Measurement of Hardness of Casted-Film-Type Capsule Film

In the evaluation of the hardness of a hard capsule, the measurement value changes depending on the capsule film thickness, in particular, the film thickness of the capsule body portion compressed by a metal indenter. In the hardness evaluation, it is important to perform the comparison using film samples having an identical thickness. Therefore, the evaluation of the hardness that depends on the composition of each hard capsule was performed by producing, instead of hard capsules formed by a dipping method, casted-films having the same compositions as those of the hard capsules by a casting method, for each composition of the hard capsule film; and evaluating these casted-films. In the following Examples, although the evaluation was performed by producing, instead of hard capsules formed by a dipping method, casted-films having the same compositions as those of the hard capsules, the casted-films ensure superior uniformity in thickness and superior reproducibility in the evaluation, thus desirably reflecting capsule film hardness improving effects.

1-1. Capsule-Preparing Solution 1-1-1. Capsule-Preparing Solution Containing HPMC as a Base As shown in Tables 3-1, 3-2, and 3-3, the following Examples generally used HPMC as a base obtained by using one kind or a mixture of two kinds of molecular weights of those having a degree of substitution of 2910 (hypromellose viscosity value=300 to 5000). As shown in the Reference Examples below, the hardness of the capsule film is independent of the hypromellose viscosity value. For the hypromellose having a degree of substitution of 2910 used in the experiments, the respective viscosity grades of Any-Coat-C series produced by Samsung (currently known as Lotte) and the respective viscosity grades of TC-5 series produced by Shin-Etsu Chemical Co., Ltd. were used for viscosity values 3, 4.5, 6, and 15, as necessary. Further, Metolose 60SH-50 produced by Shin-Etsu Chemical Co., Ltd. was used for the viscosity value of 50. Insofar as the viscosity grade value (viscosity value) was at a same level, no influence due to the difference in hypromellose manufacturer was observed.

In this embodiment, the case where the breakage resistance was not improved even by using a hypromellose viscosity value of 5000 was referred to in setting a preferred upper limit of the addition amount of the hardness improving agent. Starch decomposition products having a DE value of 4 to 100 shown in Tables 3-1, 3-2, and 3-3 were used. The Maltrin(Registered Trademark) series (GPC) was used as M100, M150, M200, and M040. The Glucidex(Registered Trademark) series (Roquette) was used as Glucidex IT38, Glucidex IT33, Glucidex IT29, Glucidex IT21, Glucidex IT19, and Glucidex 17D. The Amycol(Trademark) series (Nippon Starch Chemical Co., Ltd.) was used as Amycol No. 10. The Pinedex(Trademark) series (Matsutani Chemical Industry Co., Ltd.) was used as Pinedex #2. A titanium oxide (A100) produced by Ishikawa Sangyo Co., Ltd. was used.

The clay minerals shown in Tables 4-1 and 4-2 were used. Kunipia-F, Veegum F, Veegum HV, Veegum R, and Veegum K were used as bentonite. The Kunipia series (Kunimine Industries Co., Ltd.) was used as Kunipia-F. Veegum F, Veegum HV, Veegum R, and Veegum K (R.T. Vanderbilt C., Inc. (USA)) were used. Kaolin (K-2-500) produced by Thermo Fisher Scientific was used. Talc (Micro Ace P-3) produce by Nippon Talc Co., Ltd. was used. κ-carrageenan (SWG-J) produced by CP Kelco was used.

The Gohsenol(Trademark) series EG-18P produced by the Nippon Synthetic Chemical Industry was used as PVA.

(1) Composition

The following concentrations of the film components of a hard capsule (hydroxypropylmethylcellulose, starch decomposition product or clay mineral, gelling agent, gelling aid, and titanium oxide), excluding water, are denoted by wt % relative to 100% of the total weight after the addition of water as a solvent. The concentrations of the film components of the hard capsule, excluding water, were suitably adjusted to fall within a range of 10 to 25 wt %, in order to obtain a cast film of a desired thickness. Tables 3-1, 3-2, 3-3, 4-1, 4-2, 5, 6, and 7 show the amounts of the respective components based on 100 wt % of the total capsule film components, excluding moisture.

(2) Production of Preparing Solution

Carrageenan and potassium chloride were added to purified water and dispersed by stirring, and heated to 80° C.; thereafter, the dissolution of the materials was confirmed. Then, a starch decomposition product or a clay mineral was added. Dissolution of the starch decomposition product or dispersion of the clay mineral was confirmed. Thereafter, titanium oxide was added and dispersed sufficiently evenly by stirring. Thereafter, while keeping the liquid temperature at 80° C., HPMC was added and dispersed; the mixture was then allowed to stand for 30 minutes, and air bubbles were removed by vacuum deaeration.

Subsequently, the mixture was cooled to 50° C. to 60° C. while stirring with a three-one motor; and then stirred with a three-one motor for an hour, thereby preparing a jelly-like capsule-preparing solution.

1-1-2. Capsule-Preparing Solution Containing PVA as a Base

Carrageenan, potassium chloride, PVA, and a starch decomposition product were added to purified water at room temperature, and dispersed by stirring. After the mixture was heated to 80° C., the dissolution of the materials was confirmed. After subjecting the mixture to vacuum deaeration, the mixture was kept warm at 55° C. overnight to remove air bubbles, thereby obtaining a uniform capsule-preparing solution (immersion liquid).

Further, a clay mineral was dispersed in purified water at room temperature while stirring it with a homogenizer. Carrageenan, potassium chloride, and PVA were added and dispersed by stirring, and heated to 80° C. After subjecting the mixture to vacuum deaeration, the mixture was kept warm at 55° C. overnight to remove air bubbles, thereby obtaining a uniform capsule-preparing solution (immersion liquid).

1-2. Method for Forming Film

To obtain a casted-film, a metallic applicator was set on a glass surface or a PET film kept at room temperature; and a capsule-preparing solution of 50° C. to 60° C. was poured and moved at a constant speed, thereby producing a 100 μm uniform film. Thereafter, the hypromellose film was dried at a temperature ranging from room temperature to 30° C. for about 10 hours, and the PVA film was dried at 80° C. for about two hours. To ensure a uniform film thickness of 100 μm, an applicator having a gap of 0.4 mm to 1.5 mm was used as necessary.

1-3. Hardness Evaluation

The prepared casted-film was cut into a 10 mm×50 mm strip, and the humidity thereof was adjusted by placing it under a humidity-controlled environment of 25° C. and a relative humidity of 43% (saturated potassium carbonate aqueous solution) for a week; thereafter, the hardness was evaluated by a compression test.

The hardness evaluation was performed by setting the moisture-controlled film curved into an arch shape in the holder of an Autograph (AGS-J: Shimadzu Corporation) (as shown in FIG. 1a, the film set in the holder had a width of 2 cm and a height of 2 cm). 5- to 8-mm film top was compressed with a metal indenter (FIG. 2b), and the peak of the compression test force of the film was determined (FIG. 2c). The compression speed is, for example, 50 ram/min, and the diameter of the metallic indenter is 9 mm (FIG. 2b). The state of applying the compression test force to the body portion of a hard capsule was thus simulatively reproduced.

The measured compressive stress of each casted-film was compared with the value of the compression test force of a reference standard (a casted-film produced using the same components as those of the test specimen except for the hardness improving agent, and containing the base in an amount increased by an amount corresponding to the amount of the hardness improving agent), thereby evaluating the hardness. The compression test force of the reference standard was assumed as 100, and a value of 110 or more was regarded as an improvement in hardness. Further, a value of less than 110 was evaluated as no improvement in hardness. In Tables 3-1, 3-2, 3-3, 4-1, 4-2, 5, 6 and 7, "o" indicates an improvement in hardness, and "x" indicates no improvement in hardness. The composition of the reference standard was identical in all cases shown in Tables 3-1, 3-2, 3-3, 4-1, 4-2, 5, and 6. The hardness improving effects of a casted-film observed by such a comparison based on a reference standard is also confirmed in a capsule.

1-4. Brittleness Evaluation

The brittleness of the casted-film was determined depending on the generation of cracks when the casted-film was lightly bent. Since cracks are easily generated on such a brittle film when the film is curved into an arch shape during the compression test, or when even a slight compression test force was exerted, an accurate measurement of compression test force was difficult.

2. Test Example: Measurement of Hardness of Capsule Film Foiled into a Capsule 2-1. Method for Forming Capsule A size-2 hypromellose or PVA capsule was formed by a cold gelation method of an immersion method using a capsule-preparing solution prepared in Test Example 1 described in Section "1-1. Capsule-Preparing Solution" above.

More specifically, a capsule-forming pin at a room temperature or a similar temperature was immersed in a capsule-preparing solution (immersion liquid) adjusted to 45 to 60° C. Subsequently, the immersed pin was drawn from the immersion liquid, and air-cooled at room temperature for 20 to 90 seconds; accordingly, the capsule-preparing solution (immersion liquid) adhered to the outer surface of the pin was gelled, thereby forming a film. Further, the film was allowed to stand for 45 to 90 minutes at room temperature to dry. The capsule film thus formed was removed from the pin, and cut into a predetermined length. Thereafter, the cap and the body were bonded, and subjected to secondary drying. The secondary drying was performed for 30 minutes at around 30° C. For a capsule containing PVA as a major base ingredient, the drying after the dipping was performed at a temperature of 80 to 150° C.

2-2. Hardness Evaluation

The prepared capsule was controlled in humidity by being placed under a humidity control environment of 25° C. and a relative humidity of 43% (saturated potassium carbonate aqueous solution) for a week; thereafter, the hardness was evaluated by a compression test.

To evaluate the hardness of the capsule, the body portion of the capsule thus controlled in humidity was set in an Autograph (AGS-J: Shimadzu Corporation) (FIGS. 3a and 3b), and compressed by a metal indenter (FIG. 3a), thereby determining the compression test force value at a compression depth of 3 mm. The compression speed was 10 ram/min (FIG. 3a). The compression by a metal indenter was performed on a portion of the capsule from 3.4 to 7.9 mm from the cut end of the capsule.

2-3. Results of Hardness Evaluation of Examples, Comparative Examples, and Reference Examples (1) Casted-Film Containing Starch Decomposition Product Tables 3-1, 3-2, and 3-3 show results of hardness measurement of casted-films containing a starch decomposition product as a hardness improving agent. It was revealed that when a starch decomposition product having a DE value of 38 to 13 was added so that its content fell within a range of 10 to 30 wt %, the hardness of the casted-film became superior to that of the reference standard (Examples 1-1 to 1-32). In contrast, improvement in hardness was not observed when a starch decomposition product having a DE value of 40 or more was solely added to the film (Comparative Examples 1-1 to 1-3). Similarly, improvement in hardness was also not observed when a starch decomposition product having a DE value of 11 or less was solely added to the film (Comparative Examples 1-4 to 1-9). The results showed that a starch decomposition product having a DE value of more than 11 and less than 40 has an effect of improving the strength of the capsule film of a hard capsule. On the other hand, improvement in hardness was not observed in Comparative Examples 1-10 in which a combination of a glucose (monosaccharide) and Glucidex IT6 having a DE value of 6, thus having a calculated DE value of 29, was added to a casted-film. In contrast, an improvement in hardness was observed in Comparative Example 1-33 in which a mixed starch decomposition product, which is a mixture of maltose (disaccharide) having a DE value of 50 and Glucidex IT6 having a DE value of 6, thus having a calculated DE value of 29, was added to a casted-film. Further, an improvement in hardness was also observed in Comparative Example 1-34 in which a mixed starch decomposition product, which is a mixture of maltose (disaccharide) having a DE value of 50 and Glucidex IT6 having a DE value of 6, thus having a calculated DE value of 13, was added to a casted-film. It was regarded from the results that the hardness of the capsule film cannot be improved by the addition of monosaccharides. Furthermore, although the starch decomposition product having a DE value of 50 and a starch decomposition product having a DE value of 6 do not ensure a hardness improving effect individually, they become capable of improving the hardness of the capsule film of a hard capsule when they are added to a capsule film as a mixture having a calculated DE value of more than 11 and less than 40. In the Examples shown in Table 3, the films did not break even when they were bent as shown in FIG. 2, thereby making evaluation of film hardness possible.

TABLE 3-1

| Formulation | Viscosity Value | Reference Standard | Co. Ex. 1-1 | Co. Ex. 1-2 | Co. Ex. 1-3 | Ex. 1-1 | Ex. 1-2 | Ex. 1-3 | Ex. 1-4 |
|---|---|---|---|---|---|---|---|---|---|
| Hypromellose (Proportion (Parts by Weight) Based on Total Hypromellose Amount = 100) | 3 mPa · s | | | | | | | | |
| | 4.5 mPa · s | 80 | | | | | | | |
| | 6 mPa · s | 20 | 80 | 80 | 80 | 80 | 80 | 20 | |
| | 15 mPa · s | | 20 | 20 | 20 | 20 | 20 | 80 | 100 |
| Hypromellose Viscosity Value | | 480 | 780 | 780 | 780 | 780 | 780 | 1320 | 1500 |
| Hypromellose (wt %) | | BN | BN | BN | BN | BN | BN | BN | BN |
| κ-Carrageenan (wt %) | | 0.4 | 0.4 | 0.4 | 0.4 | 0.4 | 0.4 | 0.4 | 0.4 |
| Potassium Chloride (wt %) | | 0.65 | 0.65 | 0.65 | 0.65 | 0.65 | 0.65 | 0.65 | 0.65 |
| Titanium Oxide (wt %) | | 6 | 3 | 3 | 3 | 3 | 3 | 3 | 3 |
| Starch Decomposition Product (wt %) | Glucose | | 15 | | | | | | |
| | Maltose | | | 15 | | | | | |
| | Pinedex #6 | | | | 15 | | | | |
| | Glucidex IT38 | | | | | 10 | 15 | 20 | 30 |
| | Glucidex IT33 | | | | | | | | |
| | Glucidex IT29 | | | | | | | | |

TABLE 3-1-continued

| Formulation | | Co. Ex. 1-1 | Ex. 1-1 | Ex. 1-2 | Ex. 1-3 | Ex. 1-4 | | | |
|---|---|---|---|---|---|---|---|---|---|
| Starch Decomposition Product (wt %) (continued) | M250 | | | | | | | | |
| | Glucidex IT21 | | | | | | | | |
| | M200 | | | | | | | | |
| | Glucidex IT19 | | | | | | | | |
| | Glucidex 17D | | | | | | | | |
| | M150 | | | | | | | | |
| | Amycol No. 10 | | | | | | | | |
| | Pinedex #2 | | | | | | | | |
| | M100 | | | | | | | | |
| | Glucidex 9 | | | | | | | | |
| | Glucidex IT6 | | | | | | | | |
| | M040 | | | | | | | | |
| DE Value of Starch Decomposition Product (Calculated DE Value When Two Kinds Are Mixed) | | 0 | 100 | 50 | 40 | 38 | 38 | 38 | 38 |
| Hardness | | 100 | 72 | 84 | 95 | 110 | 111 | 120 | 120 |
| Hardness Evaluation | | | x | x | x | ○ | ○ | ○ | ○ |

| Formulation | Viscosity Value | Ex. 1-5 | Ex. 1-6 | Ex. 1-7 | Ex. 1-8 | Ex. 1-9 | Ex. 1-10 | Ex. 1-11 |
|---|---|---|---|---|---|---|---|---|
| Hypromellose (Proportion (Parts by Weight) Based on Total Hypromellose Amount = 100) | 3 mPa·s | | | | | | | |
| | 4.5 mPa·s | | | | | | | |
| | 6 mPa·s | 80 | 20 | | 80 | 80 | 20 | 80 |
| | 15 mPa·s | 20 | 80 | 100 | 20 | 20 | 80 | 20 |
| Hypromellose Viscosity Value | | 780 | 1320 | 1500 | 780 | 780 | 1320 | 780 |
| Hypromellose (wt %) | | BN | BN | BN | BN | BN | BN | BN |
| κ-Carrageenan (wt %) | | 0.4 | 0.4 | 0.4 | 0.4 | 0.4 | 0.4 | 0.4 |
| Potassium Chloride (wt %) | | 0.65 | 0.65 | 0.65 | 0.65 | 0.65 | 0.65 | 0.65 |
| Titanium Oxide (wt %) | | 3 | 3 | 3 | 3 | 3 | 3 | 3 |
| Starch Decomposition Product (wt %) | Glucose | | | | | | | |
| | Maltose | | | | | | | |
| | Pinedex #6 | | | | | | | |
| | Glucidex IT38 | | | | | | | |
| | Glucidex IT33 | 10 | 15 | 30 | | | | |
| | Glucidex IT29 | | | | 10 | 15 | 20 | |
| | M250 | | | | | | | 10 |
| | Glucidex IT21 | | | | | | | |
| | M200 | | | | | | | |
| | Glucidex IT19 | | | | | | | |
| | Glucidex 17D | | | | | | | |
| | M150 | | | | | | | |
| | Amycol No. 10 | | | | | | | |
| | Pinedex #2 | | | | | | | |
| | M100 | | | | | | | |
| | Glucidex 9 | | | | | | | |
| | Glucidex IT6 | | | | | | | |
| | M040 | | | | | | | |
| DE Value of Starch Decomposition Product (Calculated DE Value When Two Kinds Are Mixed) | | 33 | 33 | 33 | 29 | 29 | 29 | 25 |
| Hardness | | 110 | 117 | 121 | 112 | 112 | 121 | 110 |
| Hardness Evaluation | | ○ | ○ | ○ | ○ | ○ | ○ | ○ |

Ex.: Example
Co. Ex.: Comparative Example
BN: Balance

TABLE 3-2

| Formulation | Viscosity Value | Ex. 1-12 | Ex. 1-13 | Ex. 1-14 | Ex. 1-15 | Ex. 1-16 | Ex. 1-17 | Ex. 1-18 | Ex. 1-19 |
|---|---|---|---|---|---|---|---|---|---|
| Hypromellose (Proportion (Parts by Weight) Based on Total Hypromellose Amount = 100) | 3 mPa·s | | | | | | | | |
| | 4.5 mPa·s | | | | | | | | |
| | 6 mPa·s | 80 | 80 | 80 | 20 | | 80 | 80 | 20 |
| | 15 mPa·s | 20 | 20 | 20 | 80 | 100 | 20 | 20 | 80 |
| Hypromellose Viscosity Value | | 780 | 780 | 780 | 1320 | 1500 | 780 | 780 | 1320 |
| Hypromellose (wt %) | | BN | BN | BN | BN | BN | BN | BN | BN |
| κ-Carrageenan (wt %) | | 0.4 | 0.4 | 0.4 | 0.4 | 0.4 | 0.4 | 0.4 | 0.4 |
| Potassium Chloride (wt %) | | 0.65 | 0.65 | 0.65 | 0.65 | 0.65 | 0.65 | 0.65 | 0.65 |
| Titanium Oxide (wt %) | | 3 | 3 | 3 | 3 | 3 | 3 | 3 | 3 |

TABLE 3-2-continued

| Formulation | | Ex. 1-13 | Ex. 1-14 | Ex. 1-15 | Ex. 1-16 | Ex. 1-17 | Ex. 1-18 | Ex. 1-19 |
|---|---|---|---|---|---|---|---|---|
| Starch Decomposition Product (wt %) | Glucose | | | | | | | |
| | Maltose | | | | | | | |
| | Pinedex #6 | | | | | | | |
| | Glucidex IT38 | | | | | | | |
| | Glucidex IT33 | | | | | | | |
| | Glucidex IT29 | | | | | | | |
| | M250 | 15 | | | | | | |
| | Glucidex IT21 | | 10 | 15 | 20 | 30 | | |
| | M200 | | | | | | 10 | 15 | 20 |
| | Glucidex IT19 | | | | | | | |
| | Glucidex 17D | | | | | | | |
| | M150 | | | | | | | |
| | Amycol No. 10 | | | | | | | |
| | Pinedex #2 | | | | | | | |
| | M100 | | | | | | | |
| | Glucidex 9 | | | | | | | |
| | Glucidex IT6 | | | | | | | |
| | M040 | | | | | | | |
| DE Value of Starch Decomposition Product (Calculated DE Value When Two Kinds Are Mixed) | | 25 | 21 | 21 | 21 | 21 | 20 | 20 | 20 |
| Hardness | | 110 | 117 | 113 | 114 | 120 | 110 | 112 | 116 |
| Hardness Evaluation | | ○ | ○ | ○ | ○ | ○ | ○ | ○ | ○ |

| Formulation | Viscosity Value | Ex. 1-20 | Ex. 1-21 | Ex. 1-22 | Ex. 1-23 | Ex. 1-24 | Ex. 1-25 | Ex. 1-26 |
|---|---|---|---|---|---|---|---|---|
| Hypromellose (Proportion (Parts by Weight) Based on Total Hypromellose Amount = 100) | 3 mPa·s | | | | | | | |
| | 4.5 mPa·s | | | | | | | |
| | 6 mPa·s | 80 | 80 | 80 | 80 | 80 | 80 | 20 |
| | 15 mPa·s | 20 | 20 | 20 | 20 | 20 | 20 | 80 |
| Hypromellose Viscosity Value | | 780 | 780 | 780 | 780 | 780 | 780 | 1320 |
| Hypromellose (wt %) | | BN | BN | BN | BN | BN | BN | BN |
| κ-Carrageenan (wt %) | | 0.4 | 0.4 | 0.4 | 0.4 | 0.4 | 0.4 | 0.4 |
| Potassium Chloride (wt %) | | 0.65 | 0.65 | 0.65 | 0.65 | 0.65 | 0.65 | 0.65 |
| Titanium Oxide (wt %) | | 3 | 3 | 3 | 3 | 3 | 3 | 3 |
| Starch Decomposition Product (wt %) | Glucose | | | | | | | |
| | Maltose | | | | | | | |
| | Pinedex #6 | | | | | | | |
| | Glucidex IT38 | | | | | | | |
| | Glucidex IT33 | | | | | | | |
| | Glucidex IT29 | | | | | | | |
| | M250 | | | | | | | |
| | Glucidex IT21 | | | | | | | |
| | M200 | | | | | | | |
| | Glucidex IT19 | 10 | 15 | | | | | |
| | Glucidex 17D | | | 10 | 15 | | | |
| | M150 | | | | | 10 | 15 | 20 |
| | Amycol No. 10 | | | | | | | |
| | Pinedex #2 | | | | | | | |
| | M100 | | | | | | | |
| | Glucidex 9 | | | | | | | |
| | Glucidex IT6 | | | | | | | |
| | M040 | | | | | | | |
| DE Value of Starch Decomposition Product (Calculated DE Value When Two Kinds Are Mixed) | | 19 | 19 | 17 | 17 | 15 | 15 | 15 |
| Hardness | | 110 | 117 | 114 | 114 | 110 | 114 | 114 |
| Hardness Evaluation | | ○ | ○ | ○ | ○ | ○ | ○ | ○ |

Ex.: Example
BN: Balance

TABLE 3-3

| Formulation | Viscosity Value | Ex. 1-27 | Ex. 1-28 | Ex. 1-29 | Ex. 1-30 | Ex. 1-31 | Ex. 1-32 | Co. Ex. 1-4 | Co. Ex. 1-5 |
|---|---|---|---|---|---|---|---|---|---|
| Hypromellose (Proportion (Parts by Weight) Based on Total Hypromellose Amount = 100) | 3 mPa·s | | | | | | | | |
| | 4.5 mPa·s | | | | | | | | |
| | 6 mPa·s | | 80 | 80 | 80 | 20 | | 80 | 80 |
| | 15 mPa·s | 100 | 20 | 20 | 20 | 80 | 100 | 20 | 20 |

TABLE 3-3-continued

| | | | | | | | | |
|---|---|---|---|---|---|---|---|---|
| Hypromellose Viscosity Value | 1500 | 780 | 780 | 780 | 1320 | 1500 | 780 | 780 |
| Hypromellose (wt %) | BN | BN | BN | BN | BN | BN | BN | BN |
| κ-Carrageenan (wt %) | 0.4 | 0.4 | 0.4 | 0.4 | 0.4 | 0.4 | 0.4 | 0.4 |
| Potassium Chloride (wt %) | 0.65 | 0.65 | 0.65 | 0.65 | 0.65 | 0.65 | 0.65 | 0.65 |
| Titanium Oxide (wt %) | 3 | 3 | 3 | 3 | 3 | 3 | 3 | 3 |
| Starch Decomposition Product (wt %) — Glucose | | | | | | | | |
| Maltose | | | | | | | | |
| Pinedex #6 | | | | | | | | |
| Glucidex IT38 | | | | | | | | |
| Glucidex IT33 | | | | | | | | |
| Glucidex IT29 | | | | | | | | |
| M250 | | | | | | | | |
| Glucidex IT21 | | | | | | | | |
| M200 | | | | | | | | |
| Glucidex IT19 | | | | | | | | |
| Glucidex 17D | | | | | | | | |
| M150 | 30 | | | | | | | |
| Amycol No. 10 | | 5 | 10 | 15 | 20 | 30 | | |
| Pinedex #2 | | | | | | | 15 | |
| M100 | | | | | | | | 15 |
| Glucidex 9 | | | | | | | | |
| Glucidex IT6 | | | | | | | | |
| M040 | | | | | | | | |
| DE Value of Starch Decomposition Product (Calculated DE Value When Two Kinds Are Mixed) | 15 | 13 | 13 | 13 | 13 | 13 | 11 | 10 |
| Hardness | 114 | 112 | 110 | 114 | 118 | 119 | 106 | 109 |
| Hardness Evaluation | ○ | ○ | ○ | ○ | ○ | ○ | x | x |

| Formulation | Viscosity Value | Co. Ex. 1-6 | Co. Ex. 1-7 | Co. Ex. 1-8 | Co. Ex. 1-9 | Co. Ex. 1-10 | Ex. 1-33 | Ex. 1-34 |
|---|---|---|---|---|---|---|---|---|
| Hypromellose (Proportion (Parts by Weight) Based on Total Hypromellose Amount = 100) | 3 mPa·s | | | | | | | |
| | 4.5 mPa·s | | | | | | | |
| | 6 mPa·s | 80 | 20 | 80 | 80 | 80 | 80 | 80 |
| | 15 mPa·s | 20 | 80 | 20 | 20 | 20 | 20 | 20 |
| Hypromellose Viscosity Value | | 780 | 1320 | 780 | 780 | 780 | 780 | 780 |
| Hypromellose (wt %) | | BN | BN | BN | BN | BN | BN | BN |
| κ-Carrageenan (wt %) | | 0.4 | 0.4 | 0.4 | 0.4 | 0.4 | 0.4 | 0.4 |
| Potassium Chloride (wt %) | | 0.65 | 0.65 | 0.65 | 0.65 | 0.65 | 0.65 | 0.65 |
| Titanium Oxide (wt %) | | 3 | 3 | 3 | 3 | 3 | 3 | 3 |
| Starch Decomposition Product (wt %) | Glucose | | | | | 3.675 | | |
| | Maltose | | | | | | 7.84 | 2.39 |
| | Pinedex #6 | | | | | | | |
| | Glucidex IT38 | | | | | | | |
| | Glucidex IT33 | | | | | | | |
| | Glucidex IT29 | | | | | | | |
| | M250 | | | | | | | |
| | Glucidex IT21 | | | | | | | |
| | M200 | | | | | | | |
| | Glucidex IT19 | | | | | | | |
| | Glucidex 17D | | | | | | | |
| | M150 | | | | | | | |
| | Amycol No. 10 | | | | | | | |
| | Pinedex #2 | | | | | | | |
| | M100 | | | | | | | |
| | Glucidex 9 | 15 | 20 | | | | | |
| | Glucidex IT6 | | | 15 | | 11.325 | 7.16 | 12.61 |
| | M040 | | | | 15 | | | |
| DE Value of Starch Decomposition Product (Calculated DE Value When Two Kinds Are Mixed) | | 9 | 9 | 6 | 4 | 29 | 29 | 13 |
| Hardness | | 107 | 104 | 103 | 106 | 95 | 117 | 115 |
| Hardness Evaluation | | x | x | x | x | x | ○ | ○ |

Ex.: Example
Co. Ex.: Comparative Example
BN: Balance

(2) Casted-Film Containing Clay Mineral

Tables 4-1 shows the results of hardness measurement of casted-films containing a clay mineral as a hardness improving agent. With regard to bentonite, it was revealed that when Kunipia-F in an amount of 1 to 8 wt % was added, the hardness of the film was improved (Examples 2-1 to 2-12). In contrast, an improvement in hardness was not observed in a casted-film containing 0.5 wt % of bentonite (Comparative Example 2-1). With regard to kaolin, the hardness of the casted-film was improved when kaolin in an amount of 11 to 40 was added (Examples 2-13 to 2-16). In contrast, an improvement in hardness was not observed in a casted-film containing kaolin in an amount of 8 wt % or less (Comparative Examples 2-3 to 2-5). In the Examples shown in Table 4, the casted-films did not break even when they were bent as shown in FIG. 2, thereby making evaluation of film hardness possible.

Further, the tendency of easy film breakage became more significant when an excessive amount of a clay mineral was added. The casted-film containing bentonite in an amount of 10 wt % or more, or a casted-film containing kaolin or talc in an amount of more than 50 wt % was particularly easy to break, and had a difficulty in hardness evaluation. Further, the hardness of the casted-film was not improved when an inorganic filler, such as calcium citrate fine powder, calcium silicate (PS-10: Tomita Pharmaceutical Co., Ltd.), super-light synthetic aluminum silicate, or light anhydrous silicic acid (AEROSIL(Registered Trademark) 200FAD: Nippon Aerosil Co., Ltd.), which was not a clay mineral, was added (Table 4-2).

The results showed that it was possible to improve the hardness of the capsule film of a hard capsule by adding a predetermined amount of the specific clay mineral of the present invention.

TABLE 4-1

| Formulation | Viscosity Value | Co. Ex. 2-1 | Ex. 2-1 | Ex. 2-2 | Ex. 2-3 | Ex. 2-4 | Ex. 2-5 | Co. Ex. 2-2 |
|---|---|---|---|---|---|---|---|---|
| Hypromellose | 3 mPa·s | | | | | | | |
| (Proportion | 4.5 mPa·s | | | | | | | |
| (Parts by Weight) | 6 mPa·s | 80 | 80 | 80 | 80 | | 70 | 80 |
| Based on Total | 15 mPa·s | 20 | 20 | 20 | 20 | 100 | 30 | 20 |
| Hypromellose | 50 mPa·s | | | | | | | |
| Amount = 100) | | | | | | | | |
| Hypromellose Viscosity Value | | 780 | 780 | 780 | 780 | 1500 | 870 | 780 |
| κ-Carrageenan | | 0.4 | 0.4 | 0.4 | 0.4 | 0.4 | 0.4 | 0.4 |
| Potassium Chloride | | 0.65 | 0.65 | 0.65 | 0.65 | 0.65 | 0.65 | 0.65 |
| Titanium Oxide | | 6 | 3 | 3 | 3 | 3 | 3 | 3 |
| Kunipia-F | | 0.5 | 1 | 3 | 5 | 8 | | |
| Veegum F | | | | | | | 8 | |
| Veegum HV | | | | | | | | 1 |
| Veegum R | | | | | | | | |
| Veegum K | | | | | | | | |
| Kaolin | | | | | | | | |
| Talc P-3 | | | | | | | | |
| Hardness | | 98 | 112 | 111 | 119 | 136 | 117 | 101 |
| Hardness Evaluation | | x | ○ | ○ | ○ | ○ | ○ | x |

| Formulation | Viscosity Value | Ex. 2-6 | Ex. 2-7 | Ex. 2-8 | Ex. 2-9 | Ex. 2-10 | Ex. 2-11 |
|---|---|---|---|---|---|---|---|
| Hypromellose | 3 mPa·s | | | 60 | 60 | | |
| (Proportion | 4.5 mPa·s | | | | | | |
| (Parts by Weight) | 6 mPa·s | 80 | 80 | | | 80 | 80 |
| Based on Total | 15 mPa·s | 20 | 20 | 40 | 40 | 20 | 20 |
| Hypromellose | 50 mPa·s | | | | | | |
| Amount = 100) | | | | | | | |
| Hypromellose Viscosity Value | | 780 | 780 | 780 | 780 | 780 | 780 |
| κ-Carrageenan | | 0.4 | 0.4 | 0.4 | 0.4 | 0.4 | 0.4 |
| Potassium Chloride | | 0.65 | 0.65 | 0.65 | 0.65 | 0.65 | 0.65 |
| Titanium Oxide | | 3 | 3 | 3 | 3 | 3 | 3 |
| Kunipia-F | | | | | | | |
| Veegum F | | | | | | | |
| Veegum HV | | 3 | 5 | 8 | | | |
| Veegum R | | | | | 8 | | |
| Veegum K | | | | | | 3 | 5 |
| Kaolin | | | | | | | |
| Talc P-3 | | | | | | | |
| Hardness | | 114 | 112 | 120 | 113 | 110 | 116 |
| Hardness Evaluation | | ○ | ○ | ○ | ○ | ○ | ○ |

| Formulation | Viscosity Value | Ex. 2-12 | Co. Ex. 2-3 | Co. Ex. 2-4 | Co. Ex. 2-5 | Ex. 2-13 | Ex. 2-14 | Ex. 2-15 | Ex. 2-16 | Ex. 2-17 | Ex. 2-18 | Ex. 2-19 | Ex. 2-20 |
|---|---|---|---|---|---|---|---|---|---|---|---|---|---|
| Hypromellose | 3 mPa·s | 60 | | | | | | | | | | | |
| (Proportion | 4.5 mPa·s | | | | | | | | | | | | |
| (Parts by Weight) | 6 mPa·s | | 80 | 80 | 80 | 20 | | | | 20 | | | |
| Based on Total | 15 mPa·s | 40 | 20 | 20 | 20 | 80 | 100 | 100 | | 80 | 100 | 100 | |
| Hypromellose | 50 mPa·s | | | | | | | | 100 | | | | 100 |
| Amount = 100) | | | | | | | | | | | | | |
| Hypromellose Viscosity Value | | 780 | 780 | 780 | 780 | 1320 | 1500 | 1500 | 5000 | 1320 | 1500 | 1500 | 5000 |
| κ-Carrageenan | | 0.4 | 0.4 | 0.4 | 0.4 | 0.4 | 0.4 | 0.4 | 0.4 | 0.4 | 0.4 | 0.4 | 0.4 |

TABLE 4-1-continued

| | | | | | | | | | | | | |
|---|---|---|---|---|---|---|---|---|---|---|---|---|
| Potassium Chloride | 0.65 | 0.65 | 0.65 | 0.65 | 0.65 | 0.65 | 0.65 | 0.65 | 0.65 | 0.65 | 0.65 | 0.65 |
| Titanium Oxide | 3 | 3 | 3 | 3 | 3 | 3 | 3 | 3 | 3 | 3 | 0 | 0 |
| Kunipia-F | | | | | | | | | | | | |
| Veegum F | | | | | | | | | | | | |
| Veegum HV | | | | | | | | | | | | |
| Veegum R | | | | | | | | | | | | |
| Veegum K | 8 | | | | | | | | | | | |
| Kaolin | | 3 | 5 | 8 | 11 | 15 | 20 | 40 | | | | |
| Talc P-3 | | | | | | | | | 11 | 15 | 20 | 40 |
| Hardness | 117 | 101 | 98 | 106 | 110 | 113 | 115 | 127 | 116 | 118 | 126 | 151 |
| Hardness Evaluation | o | x | x | x | o | o | o | o | o | o | o | o |

Ex.: Example
Co. Ex.: Comparative Example
BN: Balance

TABLE 4-2

| Formulation | Viscosity Value | Reference Standard | Co. Ex. | Co. Ex. | Co. Ex. | Co. Ex. | Co. Ex. | Co. Ex. |
|---|---|---|---|---|---|---|---|---|
| Hypromellose | 3 mPa · s | | | | | | 60 | |
| (Proportion | 4.5 mPa · s | 80 | | | | | | |
| (Parts by Weight) | 6 mPa · s | 20 | 70 | 70 | 70 | | | |
| Based on Total Hypromellose Amount = 100) | 15 mPa · s | | 30 | 30 | 30 | 100 | 40 | 100 |
| Hypromellose Viscosity Value | | 480 | 870 | 870 | 870 | 1500 | 780 | 1500 |
| Hypromellose (wt %) | | BN | BN | BN | BN | BN | BN | BN |
| κ-Carrageenan (wt %) | | 0.4 | 0.4 | 0.4 | 0.4 | 0.4 | 0.4 | 0.4 |
| Potassium Chloride (wt %) | | 0.65 | 0.65 | 0.65 | 0.65 | 0.65 | 0.65 | 0.65 |
| Titanium Oxide (wt %) | | 6 | 3 | 3 | 3 | 3 | 3 | 3 |
| Calcium Citrate Fine Powder (wt %) | | | 8 | | | | | |
| PS-10 (Calcium Silicate) (wt %) | | | | 8 | | | | |
| Super-Light Synthetic Aluminum Silicate (wt %) | | | | | 8 | 15 | | |
| AEROSIL 200FAD (Light Anhydrous Silicic Acid) (wt %) | | | | | | | 8 | 15 |
| Hardness | | 100 | 104 | 94 | 97 | 98 | 96 | 91 |
| Hardness Evaluation | | | x | x | x | x | x | x |

Co. Ex.: Comparative Example
BN: Balance (3) Casted-Film Containing Starch Decomposition Product and Clay Mineral Table 5 shows results of hardness measurement of casted-films containing a starch decomposition product and a clay mineral. The hardness was improved both in Example 3-1 and Example 3-2. In particular, the improvement in hardness in Example 3-2 was superior to that of Example 2-7 shown in Table 4-1. The results showed that it was possible to further improve the hardness of the capsule film of a hard capsule by adding a combination of a starch decomposition product and a clay mineral to a capsule film. In the Examples shown in Table 5, the casted-films did not break even when they were bent as shown in FIG. 2, thereby making evaluation of film hardness possible.

TABLE 5

| Formulation | Viscosity Value | Reference Standard | Ex. 3-1 | Ex. 3-2 |
|---|---|---|---|---|
| Hypromellose | 3 mPa · s | | | |
| (Proportion | 4.5 mPa · s | 80 | | |
| (Parts by Weight) | 6 mPa · s | 20 | 30 | |
| Based on Total Hypromellose Amount = 100) | 15 mPa · s | | 70 | 100 |
| Hypromellose Viscosity Value | | 480 | 1230 | 1500 |
| Hypromellose (wt %) | | BN | BN | BN |
| κ-Carrageenan (wt %) | | 0.4 | 0.4 | 0.4 |
| Potassium Chloride (wt %) | | 0.65 | 0.65 | 0.65 |
| Titanium Oxide (wt %) | | 6 | 3 | 3 |
| DE Value and wt % of Starch Decomposition Product | DE = 29 | | 10 | |
| | DE = 20 | | | 15 |
| Veegum F (wt %) | | | 3 | |
| Veegum HV (wt %) | | | | 5 |
| Hardness | | 100 | 121 | 121 |
| Hardness Evaluation | | | o | o |

Ex.: Example
BN: Balance (4) Evaluation of Capsule Film Containing PVA as a Base The hardness improvement effects of a starch decomposition product or a clay mineral on a casted-film containing PVA as a base was evaluated. As shown in Examples 4-1 and 4-2 in Table 6, the hardness of the film was improved by addition of a starch decomposition product. Further, as shown in Examples 4-3 to 4-5, the hardness of the film was improved by the addition of a clay mineral. The results showed that a starch decomposition product and a clay mineral also improved the hardness of the capsule film of a hard capsule containing PVA as a base. In the Examples shown in Table 6, the films did not break even when they were bent as shown in FIG. 2, thereby making evaluation of film hardness possible.

TABLE 6

| Formulation | Reference Standard | Ex. 4-1 | Ex. 4-2 | Ex. 4-3 | Ex. 4-4 | Ex. 4-5 |
|---|---|---|---|---|---|---|
| PVA (EG-18P) | BN | BN | BN | BN | BN | BN |
| κ-Carrageenan | 0.4 | 0.4 | 0.4 | 1.5 | 0.4 | 0.4 |
| Potassium Chloride | 0.65 | 0.65 | 0.65 | 0.5 | 0.65 | 0.65 |
| Titanium Oxide | 0 | 0 | 0 | 0 | 0 | 0 |
| Starch Decomposition Product DE = 21 | | 15 | | | | |
| Starch Decomposition Product DE = 33 | | | 15 | | | |
| Kunipia-F (wt %) | | | | 3 | | |
| Talc (wt %) | | | | | 30 | |
| Kaolin (wt %) | | | | | | 15 |
| Hardness | 100 | 126 | 114 | 115 | 138 | 116 |
| Hardness Evaluation | | ○ | ○ | ○ | ○ | ○ |

Ex. : Example
Co. Ex. : Comparative Example
BN: Balance (5) Reference Examples

The Reference Examples shown in Table 7 indicate that no components other than starch decomposition products and clay minerals had any influence on the hardness of a capsule film. As shown in Reference Examples 7 to 12, the difference in hypromellose viscosity value had no influence on the film strength.

Further, generally, κ-carrageenan is appropriately adjusted in an amount of 0.05 to 0.5 wt %, and potassium chloride is appropriately adjusted in an amount of 0.1 to 1.5 wt %. Further, as shown in Reference Examples 1 to 5, the concentration or the presence/absence of gelling agent (carrageenan) or gelling aid (potassium chloride) had no influence on the hardness within the range of the tests performed in the present application. Further, the addition of titanium oxide also had no influence on the hardness within the range of 0 to 30 wt % (Reference Examples 1, 2, and 12 to 14).

In the casted-films of all of the Examples, the moisture content based on loss on drying after 1-week humidity control at a relative humidity of 43% and a temperature of 25° C. fell within a range of 4 to 7%, relative to the entire film weight.

TABLE 7

| Formulation | Viscosity Value | Reference Standard | Re. Ex. 1 | Re. Ex. 2 | Re. Ex. 3 | Re. Ex. 4 | Re. Ex. 5 | Re. Ex. 6 | Re. Ex. 7 |
|---|---|---|---|---|---|---|---|---|---|
| Hypromellose (Proportion (Parts by Weight) Based on Total Hypromellose Amount = 100) | 3 mPa·s | | | | | | | | 100 |
| | 4.5 mPa·s | 80 | 80 | 80 | 80 | 80 | 80 | 80 | |
| | 6 mPa·s | 20 | 20 | 20 | 20 | 20 | 20 | 20 | |
| | 15 mPa·s | | | | | | | | |
| Hypromellose Viscosity Value | | 480 | 480 | 480 | 480 | 480 | 480 | 480 | 300 |
| Hypromellose (wt %) | | BN | BN | BN | BN | BN | BN | BN | BN |
| κ-Carrageenan (wt %) | | 0.4 | 0.4 | 0.4 | 0.4 | 0.1 | 1.5 | 0.4 | 0.4 |
| Potassium Chloride (wt %) | | 0.65 | 0.65 | 0.3 | 1.0 | 0.65 | 0.65 | 0.65 | 0.65 |
| Titanium Oxide (wt %) | | 6 | 3 | 3 | 3 | 3 | 3 | 0 | 3 |
| Hardness | | 100 | 93 | 96 | 86 | 90 | 89 | 97 | 97 |
| Hardness Evaluation | | | x | x | x | x | x | x | x |
| Difference in Amount of Titanium Oxide | | A | A | | | | | A | |
| Difference in Hypromellose Viscosity Value | | | | | | | | | C |
| Difference in Amount of Gelling Agent (CA, KCL) | | | D | D | D | D | D | | |

TABLE 7-continued

| Formulation | Viscosity Value | Re. Ex. 8 | Re. Ex. 9 | Re. Ex. 10 | Re. Ex. 11 | Re. Ex. 12 | Re. Ex. 13 | Re. Ex. 14 |
|---|---|---|---|---|---|---|---|---|
| Hypromellose (Proportion (Parts by Weight) Based on Total Hypromellose Amount = 100) | 3 mPa·s | | | 60 | | | | |
| | 4.5 mPa·s | 100 | | | | | | |
| | 6 mPa·s | | 100 | | 20 | | | |
| | 15 mPa·s | | | 40 | 80 | 100 | 100 | 100 |
| Hypromellose Viscosity Value | | 450 | 600 | 780 | 1320 | 1500 | 1500 | 1500 |
| Hypromellose (wt %) | | BN | BN | BN | BN | BN | BN | BN |
| κ-Carrageenan (wt %) | | 0.4 | 0.4 | 0.4 | 0.4 | 0.4 | 0.4 | 0.4 |
| Potassium Chloride (wt %) | | 0.65 | 0.65 | 0.65 | 0.65 | 0.65 | 0.65 | 0.65 |
| Titanium Oxide (wt %) | | 3 | 3 | 3 | 3 | 3 | 15 | 30 |
| Hardness | | 100 | 101 | 99 | 101 | 99 | 100 | 102 |
| Hardness Evaluation | | x | x | x | x | x | x | x |
| Difference in Amount of Titanium Oxide | | | | | | B | B | B |
| Difference in Hypromellose Viscosity Value | | C | C | C | C | C | | |
| Difference in Amount of Gelling Agent (CA, KCL) | | | | | | | | |

Re. Ex.: Reference Example
BN: Balance
A, B (Re. Exs. 1, 6, 12, 13, and 14) shows that there is no influence on the hardness when the titanium oxide amount falls within 0 to 30%
C (Re. Exs. 7-12) shows that there is no influence on the hardness when the hypromellose viscosity value falls within 3 to 15 mPa·s.
D (Re. Exs. 1-5) shows that there is no influence on the hardness when the amount of gelling agent (CA: κ-Carrageenan) and gelling aid (KCL) fall within 0.1 to 1.5% and 0.3 to 1.0%, respectively.

The invention claimed is:

1. A hard capsule comprising a film containing a base and a hardness improving agent, wherein
the base is hydroxypropylmethylcellulose; and
the hardness improving agent is at least one member selected from the group consisting of starch decomposition products having a DE value of 13≤DE value≤38, and two or more kinds of starch decomposition product combined to have a calculated DE value of 13≤DE value≤38, provided that the two or more kinds of starch decomposition product exclude starch decomposition products solely having a DE value of 5 or less and monosaccharides.

2. The hard capsule according to claim 1, wherein the hardness improving agent is two or more kinds of starch decomposition product, and the two or more kinds of starch decomposition product are selected from starch decomposition products having a DP value of more than 5 and not more than 50.

3. The hard capsule according to claim 1, wherein the amount of the hardness improving agent contained in the hard capsule is 10 to 30 wt % based on 100 wt % of the total film components of the hard capsule, excluding moisture.

4. The hard capsule according to claim 1, further comprising a gelling agent, or a gelling agent and a gelling aid.

5. The hard capsule according to claim 4, wherein the gelling agent is κ-carrageenan, and the gelling aid is potassium chloride.

6. The hard capsule according to claim 1, further comprising a plasticizer and/or a light shielding agent.

7. The hard capsule according to claim 1, wherein the hard capsule further comprises at least one member selected from the group consisting of bentonite, talc, and kaolin.

8. A hard capsule-preparing solution comprising a base and a hardness improving agent, wherein
the base is hydroxypropylmethylcellulose; and
the hardness improving agent is at least one member selected from the group consisting of starch decomposition products having a DE value of 13≤DE value≤38, and two or more kinds of starch decomposition product combined to have a calculated DE value of 13≤DE value≤38, provided that the two or more kinds of starch decomposition product exclude starch decomposition products solely having a DE value of 5 or less and monosaccharides.

9. The hard capsule-preparing solution according to claim 8, wherein the hardness improving agent is two or more kinds of starch decomposition product, and the two or more kinds of starch decomposition product are selected from starch decomposition products having a DP value of more than 5 and not more than 50.

10. The hard capsule-preparing solution according to claim 8, wherein the amount of the hardness improving agent contained in the hard capsule is 10 to 30 wt % based on 100 wt % of the total components of the preparing solution excluding solvent.

11. The hard capsule-preparing solution according to claim 8, further comprising a gelling agent, or a gelling agent and a gelling aid.

12. The hard capsule-preparing solution according to claim 11, wherein the gelling agent is κ-carrageenan, and the gelling aid is potassium chloride.

13. The hard capsule-preparing solution according to claim 8, further comprising a plasticizer and/or a light shielding agent.

14. The hard capsule-preparing solution according to claim 8, wherein the hard capsule further comprises at least one member selected from the group consisting of bentonite, talc, and kaolin.

15. A method for preparing a hard capsule, comprising the step of:
preparing a hard capsule by using the hard capsule-preparing solution according to claim 8.

16. The method for preparing a hard capsule according to claim 15, wherein the method for preparing a hard capsule is a cold gelation method.

17. The method for preparing a hard capsule according to claim 15, wherein the method for preparing a hard capsule is a method for improving the hardness of a hard capsule.

18. The hard capsule according to claim 1, wherein
the starch decomposition product having a DE value of 13≤DE value≤38 is dextrin selected from the group consisting of amylodextrin, erythrodextrin, achrodextrin, and maltodextrin, and
the two or more kinds of starch decomposition product combined to have a calculated DE value of 13≤DE value≤38 are maltodextrin and maltose.

19. The hard capsule according to claim 4, wherein
the hard capsule comprises the gelling agent and the gelling aid, and
the amount of the gelling agent is 0.3 to 8 wt % and the amount of the gelling aid is 0.3 to 1.6 wt % based on 100 wt % of the total film components of the hard capsule, excluding moisture.

* * * * *